United States Patent
Lu et al.

(10) Patent No.: US 9,296,792 B2
(45) Date of Patent: Mar. 29, 2016

(54) ORDERED FLAGELLIN ARRAY AS AN IMMUNOSTIMULANT

(71) Applicant: The Board of Trustees of the Leland Stanford Junior University, Palo Alto, CA (US)

(72) Inventors: Yuan Lu, Palo Alto, CA (US); James Robert Swartz, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 13/901,392

(22) Filed: May 23, 2013

(65) Prior Publication Data
US 2013/0323281 A1  Dec. 5, 2013

Related U.S. Application Data

(60) Provisional application No. 61/650,887, filed on May 23, 2012.

(51) Int. Cl.
| | |
|---|---|
| A61K 45/00 | (2006.01) |
| A61K 39/385 | (2006.01) |
| C07K 14/255 | (2006.01) |
| A61K 39/39 | (2006.01) |
| A61K 39/145 | (2006.01) |
| A61K 39/12 | (2006.01) |
| A61K 39/00 | (2006.01) |

(52) U.S. Cl.
CPC ............... *C07K 14/255* (2013.01); *A61K 39/12* (2013.01); *A61K 39/145* (2013.01); *A61K 39/39* (2013.01); *A61K 2039/5258* (2013.01); *A61K 2039/55516* (2013.01); *A61K 2039/6068* (2013.01); *C07K 2319/00* (2013.01); *C12N 2730/10134* (2013.01)

(58) Field of Classification Search
None
See application file for complete search history.

(56) References Cited

U.S. PATENT DOCUMENTS

| | | | |
|---|---|---|---|
| 6,337,191 B1 | 1/2002 | Swartz et al. | |
| 7,517,520 B2 | 4/2009 | Manolova et al. | |
| 8,337,864 B2* | 12/2012 | Rhee et al. | 424/261.1 |
| 2004/0209321 A1 | 10/2004 | Swartz et al. | |
| 2005/0054032 A1 | 3/2005 | Swartz et al. | |
| 2005/0054044 A1 | 3/2005 | Swartz et al. | |
| 2007/0275416 A1* | 11/2007 | Gloeckner et al. | 435/7.5 |
| 2009/0011982 A1* | 1/2009 | Gudkov et al. | 514/12 |
| 2011/0008318 A1 | 1/2011 | Aderem et al. | |
| 2011/0110962 A1* | 5/2011 | Sirard | 424/184.1 |

(Continued)

FOREIGN PATENT DOCUMENTS

| | | |
|---|---|---|
| WO | 2004016778 | 2/2004 |
| WO | 2005052117 | 6/2005 |
| WO | 2010062757 | 6/2010 |

OTHER PUBLICATIONS

Frottin et al., "The Proteomics of N-terminal Methionine Cleavage," Mollecular and Cellular Proteomics 5: 2336-2349 (2006).*

(Continued)

*Primary Examiner* — Benjamin P Blumel
*Assistant Examiner* — M. Franco Salvoza
(74) *Attorney, Agent, or Firm* — Pamela J. Sherwood; Bozicevic, Field & Francis LLP

(57) ABSTRACT

Bacterial flagellin protein is modified to improve adjuvant activity.

10 Claims, 10 Drawing Sheets
(10 of 10 Drawing Sheet(s) Filed in Color)

(56) References Cited

U.S. PATENT DOCUMENTS

2011/0135680 A1* 6/2011 Song et al. .................. 424/193.1
2013/0202627 A1* 8/2013 Gomez Casado .......... 424/184.1

OTHER PUBLICATIONS

Jiang et al., "Reduction of Protein Degradation by Use of Protease-Deficient Mutants in Cell-Free Protein Synthesis System of *Escherichia coli*," Journal of Bioscience and Bioengineering, vol. 93, No. 2: 151-156 (2002).*
Wang et al., "Directed Evolution of Substrate-Optimized GroEL/S Chaperonins," Cell, vol. 111, 1027-1039 (2002).*
Loladze et al., "Thermodynamic Consequences of Burial of Polar and Non-polar Amino Acid Residues in the Protein Interior," J. Mol. Biol. 320: 343-357 (2002).*
Besnosov et al. "On the Multicomponent Nature of Halobacterium salinarum Flagella," Microbiology, vol. 76, No. 4: 435-441 (2007).*
Wang et al., "Processing of N-Terminal Unnatural Amino Acids in Recombinant Human Interferon-β in *Escherichia coli*," ChemBioChem 9: 324-330 (2008).*
Sitaraman et al., "High-Throughput Protein Expression Using Cell-Free System," Methods in Molecular Biology: High-Throughput Protein Expression and Purification, vol. 498 (2009).*
Sherman et al., "Methionine or Not Methionine at the Beginning of a Protein," BioEssays vol. 3, No. 1 (2005).*
Calhoun; et al. "Energizing cell-free protein synthesis with glucose metabolism", Biotechnol and Bioeng (Jun. 2005), 90(5):606-613.
Jewett; et al. "Mimicking the *Escherichia coli* cytoplasmic environment activates long-lived and efficient cell-free protein synthesis", Biotechnol and Bioeng (Apr. 2004), 86(1):19-26.
Jewett; et al. "Rapid expression and purification of 100 nmol quantities of active protein using cell-free protein synthesis", Biotechnol Prog (Jan.-Feb. 2004), 20(1):102-109.
Jewett; et al. "Prokaryotic Systems for In Vitro Expression. In: Weiner M, Lu Q, editors. Gene cloning and expression technologies", Eaton Publishing (2002), 391-411.
Lin; et al. "Genetic reconstruction of the aerobic central metabolism in *Escherichia coli* for the absolute aerobic production of succinate", Biotechnol Bioeng (Jan. 2005), 89(2):148-156.
Lin; et al. "Streamlining *Escherichia coli* S30 extract preparation for economical cell-free protein synthesis", Biotechnol Prog (Mar.-Apr. 2005), 21(2):460-465.
Patel; et al. "Surface functionalization of virus-like particles by direct conjugation using azide-alkyne click chemistry", Bioconjug Chem (Mar. 2011), 22(3):376-387.
Welsh; et al. "Multiply mutated Gaussia luciferases provide prolonged and intense bioluminescence", Biochem Biophys Res Commun (Nov. 2009), 389(4):563-568.
Zawada; et al. "Effects of growth rate on cell extract performance in cell-free protein synthesis", Biotechnol Bioeng (Jul. 2006), 94(4):618-624.

* cited by examiner

ORDERED FLAGELLIN ARRAY AS AN IMMUNOSTIMULANT

FEDERALLY SPONSORED RESEARCH AND DEVELOPMENT

This invention was made with Government support under contract A1057229 awarded by the National Institutes of Health. The Government has certain rights in this invention.

BACKGROUND OF THE INVENTION

Immune responses to resolve different pathologies, such as those seen in viral infections, bacterial infections, cancer, and allergic reactions are important to the overall health of the host. Successful resolution of infections, cancer, or allergic reactions may depend on the type and magnitude of the immune response. Immunizations, whereby antigen is used to elicit further immune responses, may be helpful in successfully resolving the infections, cancers, and/or allergic reactions. It would be desirable to have a method of immunization that would enable the immune system to address all the aforementioned infections and diseases.

While vaccination protocols have been some of the great medical achievements in the last century, there are still conditions where an effective immune response has been difficult to generate. For example, human tumor immunotherapy has met with only limited success. Among the reasons for this has been the limited availability of tumor-associated antigens, and an inability to deliver such antigens in a manner that renders them immunogenic. In other instances, the need for a fast immune response is not met by current vaccine technology.

In the continual pursuit for safer and more effective vaccines, new technologies, including recombinant, purification and synthetic methods, have been used to improve the quality and specificity of antigens used. Purified, sub-unit and synthesized antigens demonstrate increased safety but diminished immunogenicity, which has been one driver for identification of effective adjuvants. Adjuvants are generally compounds, that when administered with an antigen (either in conjunction with, or given prior to the administration of the antigen) enhances and/or modify the immune response to that particular antigen.

The present invention provides novel immunogenic compositions that exhibit improved immunogenicity; and methods of use of such compositions.

RELEVANT LITERATURE

U.S. Pat. No. 6,337,191 B1; Swartz et al. U.S. Patent Published Application 20040209321; Swartz et al. International Published Application WO 2004/016778; Swartz et al. U.S. Patent Published Application 2005-0054032-A1; Swartz et al. U.S. Patent Published Application 2005-0054044-A1; Swartz et al. International Published Application WO 2005/052117. Calhoun and Swartz (2005) Biotechnol Bioeng 90(5):606-13; Jewett and Swartz (2004) Biotechnol Bioeng 86(1):19-26; Jewett et al. (2002) Prokaryotic Systems for In Vitro Expression. In: Weiner M, Lu Q, editors. Gene cloning and expression technologies. Westborough, Mass.: Eaton Publishing. p 391-411; Lin et al. (2005) Biotechnol Bioeng 89(2):148-56; Liu et al., 2005 Biotechnol Prog 21:460-465; Jewett MC and Swartz JR, 2004 Biotechnol Prog 20:102-109; Zawada and Swartz Biotechnol Bioeng, 2006. 94(4): p. 618-24.

SUMMARY OF THE INVENTION

Polypeptide compositions that increase immunogenicity, and methods of use thereof are provided, where the immune response of a mammalian host to an antigen of interest is increased by co-formulation of the antigen with an ordered flagellin array. In some embodiments of the invention, the ordered flagellin array is presented on a virus like particle (VLP). In some embodiments the flagellin-VLP further comprises one or more antigens of interest. In other embodiments the flagellin-VLP is co-formulated with one or more antigens of interest.

The ordered flagellin array is achieved by the targeted introduction of unnatural amino acids, which unnatural amino acids are useful in forming a covalent bond to a protein of a VLP. In some embodiments, the methionine residues of the flagellin protein are substituted with the unnatural amino acid. In certain embodiments, the native methionine residues close to the TLR5 receptor binding region of flagellin, e.g. M310 and M466, are substituted with a non-polar amino acid other than methionine, e.g. A, G, V, I, L, F, etc., for example M310I, M466I, etc. In some embodiments a methionine residue suitable for substitution with an unnatural amino acid is introduced in a region distant from the TLR5 receptor binding region, e.g. residue 235-245, including without limitation G239. Alternatively, the unnatural amino acid is introduced as residue 1, where the amino acid at residue 2 is mutated to decrease removal of the terminal amino acid, e.g. A2I. In some embodiments the unnatural amino acid is homopropargylglycine. In some embodiments a modified flagellin polypeptide is provided comprising these changes. In some embodiments the polypeptide is linked to a VLP. In some embodiments a formulation comprising such a VLP and a pharmaceutically acceptable excipient is provided. In some embodiments methods for inducing an immune response to an antigen of interest are provided.

Optionally the flagellin coding sequence at the start site is modified to optimize translation efficiency, e.g. with the underline nucleotide change: ATGGCACAAGTGATT.

In other embodiments, it is surprisingly found that flagellin protein produced by cell free protein synthesis in a protease deficient reaction mixture, e.g. where the reaction mix comprises a cocktail of protease inhibitors, or where the bacterial cell extract used in the reaction mix is derived from a protease deficient organism, including without limitation *E. coli* BL21, which is deficient in the Lon and OmpT proteases. The GroEL-GroES (GroEL/S) chaperonin may be overexpressed or exogenously added to the extract for improved yield. Compositions of flagellin protein synthesized in a cell free protein synthesis reaction deficient in proteases are provided herein, which compositions have a measured TLR5 affinity higher than 10 pM. Such compositions find use, for example, as an adjuvant in place of, or in combination with, an ordered flagellin array. The flagellin protein may be isolated, admixed with immunogen, etc., and is generally provided in a pharmaceutically acceptable adjuvant.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
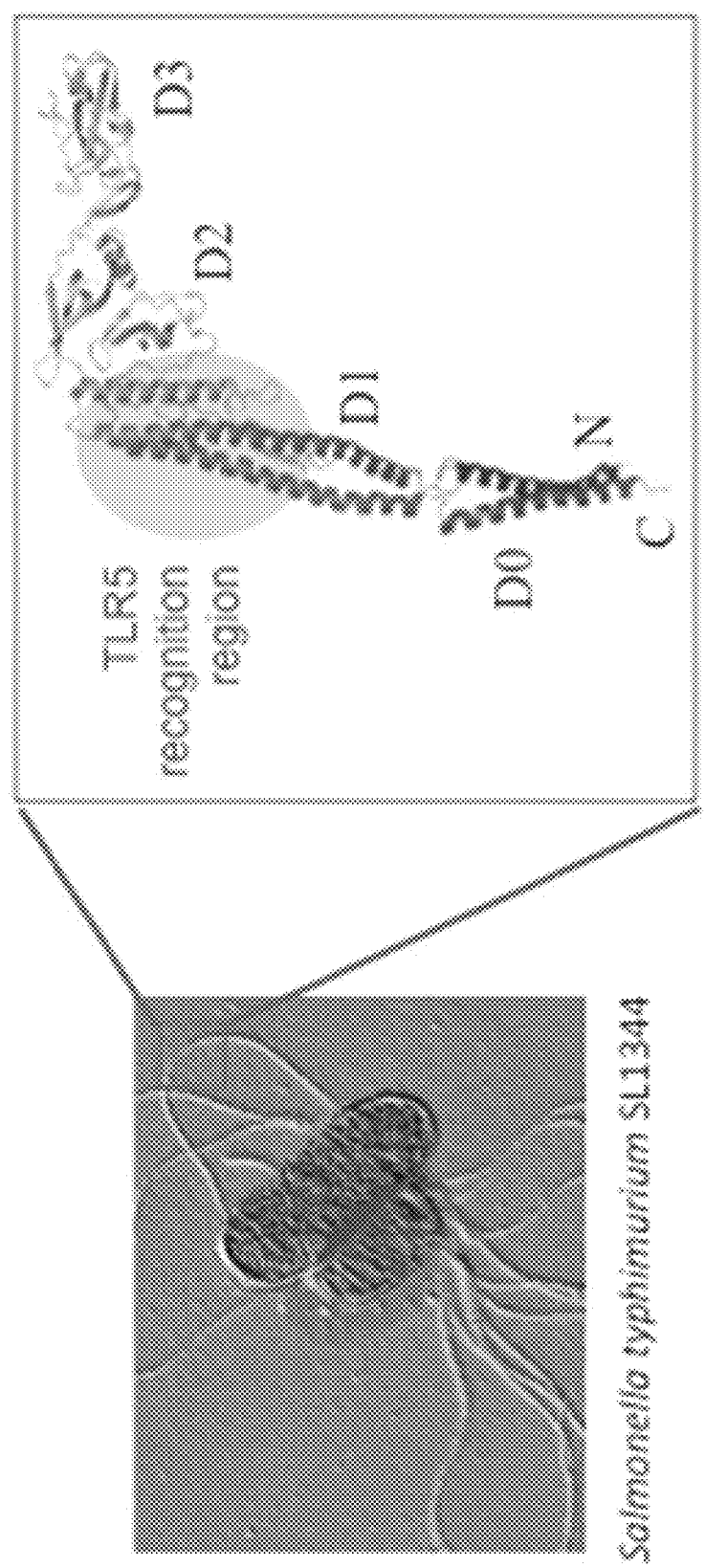
FIG. 1 Structure of flagellin.

The present invention is directed to immunogenic compositions and methods useful for the induction and/or enhancement of an immune response, which may be humoral and/or cell-mediated, in a human, a non-human animal, or cell culture, usually in a mammalian host. Immunogenic compositions of the invention comprise an ordered flagellin array as described herein; and an antigenic compound, which may be a polypeptide antigen. The presence of the ordered flagellin array enhances the immune response to the antigen. The ordered flagellin array may enhance an immune response by affecting, for example, the type and quantity of cellular responses, and/or of immunoglobulins, chemokines, and/or cytokines produced. The innate immunity, humoral and/or cell-mediated immune responses are more effective with the presence of the ordered flagellin array.

In some embodiments, the specific titer of antibodies raised in a mammalian host to an immunogen is increased at least about 20% when the immunogen is delivered with an ordered flagellin array, as compared to the immunogen when delivered by the same route in the absence of the ordered flagellin array. In other embodiments, the specific titer is increased at least about 30%, at least about 40%, at least about 50%, at least about 75%, at least about 100%, or more.

The ordered flagellin array may be provided in a composition with an antigenic compound, where the two are not covalently joined; or where the two are present on a single VLP.

Proteins for use in the invention may be purified and formulated in pharmacologically acceptable vehicles for administration to a patient. In one embodiment of the invention the fusion protein comprises at least one domain of an immunoglobulin, e.g. a variable region domain; a constant region domain; a single chain Fv fragment; etc. Such fusion proteins find use, for example, as vaccines for the treatment of B cell lymphomas.

Definitions

As used herein, the term "antigenic compound" refers to any substance that can be recognized by the immune system (e.g., bound by an antibody or processed so as to elicit a cellular immune response) under appropriate conditions.

An "antigen" as used herein includes but is not limited to cells; cell extracts; proteins; lipoproteins; glycoproteins; nucleoproteins; polypeptides; peptides; polysaccharides; polysaccharide conjugates; peptide mimics of polysaccharides; lipids; glycolipids; carbohydrates; viruses; viral extracts; bacteria; bacterial extracts; fungi; fungal extracts; multicellular organisms such as parasites; and allergens. In some embodiments of the invention the antigen is a polypeptide, e.g. a native polypeptide; a polypeptide produced by recombinant methods, including in vitro cell free synthesis, bacterial and prokaryotic expression systems; and the like. Such antigens include, without limitation, viral antigens derived from HIV; influenza, smallpox (vaccinia), measles, mumps, rubella, poliovirus, rotavirus, varicella (chickenpox), hepatitis A, B, C, D virus, bacterial antigens, tumor antigens, and the like. Bacterial antigens of interest include, without limitation, antigens derived from *Bacillus anthracis; Bordetella pertussis, Clostridium tetani, Haemophilus influenzae, Corynebacterium diphtheriae, Meningococcus* sp., *Streptococcus pneumoniae, Salmonella typhi, Mycobacterium tuberculosis*, etc.

Antigens may be exogenous (e.g., from a source other than the individual to whom the antigen is administered, e.g., from a different species) or endogenous (e.g., originating from within the host, e.g., a diseased element of body, a cancer antigen, a virus infected cell producing antigen, and the like). Antigens may be native (e.g., naturally-occurring); synthetic; or recombinant. Antigens include crude extracts; whole cells; and purified antigens, where "purified" indicates that the antigen is in a form that is enriched relative to the environment in which the antigen normally occurs and/or relative to the crude extract, for example, a cultured form of the antigen.

An "immunogenic composition" as used here in refers to a combination of two or more substances (e.g., an antigen and an immune enhancing linker) that together elicit an immune response when administered to a host.

The term "polypeptide," "peptide," "oligopeptide," and "protein," are used interchangeably herein, and refer to a polymeric form of amino acids of any length, which can include coded and non-coded amino acids, chemically, or biochemically modified or derivatized amino acids, and polypeptides having modified peptide backbones.

An "effective amount of an antigenic compound" refers to an amount of antigenic compound which, in optional combination with an adjuvant, will cause the subject to produce a specific immunological response to the antigenic compound.

The term "immune response" refers to any response to an antigenic or immunogenic compound by the immune system of a vertebrate subject. Exemplary immune responses include, but are not limited to local and systemic cellular as well as humoral immunity, such as cytotoxic T lymphocytes (CTL) responses, including antigen-specific induction of $CD8^+$ CTLs, helper T-cell responses including T-cell proliferative responses and cytokine release, and B-cell responses including antibody responses.

The term "eliciting an immune response" is used herein generally to encompass induction and/or potentiation of an immune response.

The term "inducing an immune response" refers to an immune response that is stimulated, initiated, or induced.

The term "potentiating an immune response" refers to a pre-existing immune response that is improved, furthered, supplemented, amplified, enhanced, increased, or prolonged.

The expression "enhanced immune response" or similar means that the immune response is elevated, improved, or enhanced to the benefit of the host relative to the prior immune response status, for example, before the administration of an immunogenic composition of the invention.

The terms "humoral immunity" and "humoral immune response" refer to the form of immunity in which antibody molecules are produced in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

The term "immunogenic amount" refers to an amount of antigenic compound sufficient to stimulate an immune response, when administered with a subject immunogenic composition, as compared with the immune response elicited by the antigen in the absence of the polynucleotide adjuvant.

The term "immunopotentiating amount" refers to the amount of the adjuvant needed to effect an increase in antibody titer and/or cell-mediated immunity when administered with an antigenic compound in a composition of the invention, as compared with the increase in antibody and/or cell mediated immunity level observed in the absence of the polynucleotide adjuvant.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a mammalian subject, more particularly a human, and includes: (a) preventing the disease or symptom from occurring in a subject which may be predisposed to the disease or symptom but has not yet been diagnosed as having it; (b) inhibiting the disease symptom, e.g., arresting its development; or relieving the disease symptom, i.e., causing regression of the disease or symptom (c) reduction of a level of a product produced by the infectious agent of a disease (e.g., a toxin, an antigen, and the like); and (d) reducing an undesired physiological response to the infectious agent of a disease (e.g., fever, tissue edema, and the like).

Virus Like Particle. As used herein, the term "virus like particle" refers to a stable macromolecular assembly of one or more virus proteins, usually viral coat proteins. The number of separate protein chains in a VLP will usually be at least about 60 proteins, about 80 proteins, at least about 120 proteins, or more, depending on the specific viral geometry. In the methods of the invention, the cell-free synthesis reaction mixture provides conditions permissive for self-assembly into the capsid structure, even where the concentration of coat proteins may be dilute relative to the concentrations associated with in vivo viral synthesis.

A stable VLP maintains the association of proteins in a capsid structure under physiological conditions for extended periods of time, e.g. for at least about 24 hrs, at least about 1 week, at least about 1 month, or more. A feature of the stable attachment of flagellin to the VLP is that, once assembled, the flagellin linked VLP can have a stability commensurate with the native virus particle, e.g. upon exposure to pH changes, heat, freezing, ionic changes, etc. In some embodiments there is sufficient antigen in a flagellin fusion protein and/or adjuvant molecules on the surface of the VLP so that when a VLP preparation is formulated into an immunogenic composition and administered to an animal or human, an immune response (cell-mediated or humoral) is raised.

Unnatural Amino Acids. Examples of unnatural amino acids that can be used in the methods of the invention include: an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; a cyclic amino acid other than proline, etc.

Unnatural amino acids of interest include, without limitation, amino acids that provide a reactant group for CLICK chemistry reactions (see *Click Chemistry: Diverse Chemical Function from a Few Good Reactions* Hartmuth C. Kolb, M. G. Finn, K. Barry Sharpless Angewandte Chemie International Edition Volume 40, 2001, P. 2004, herein specifically incorporated by reference). For example, the amino acids homopropargylglycine (HPG), p-acetyl-L-phenylalanine, p-propargyloxyphenylalanine, and p-azido-L-phenylalanine are of interest.

Polypeptides

The ordered flagellin array is achieved by the targeted modification of a wild-type flagellin protein, including specifically the amino acid sequence of SEQ ID NO:1, to provide for targeted introduction of an unnatural amino acid, which unnatural amino acids are useful in forming a covalent bond to a protein of a VLP.

In some embodiments, methionine residues of the flagellin protein are substituted with the unnatural amino acid. Methionines for substitution may be naturally occurring, particularly M1; or may be introduced. In some embodiments a methionine residue suitable for substitution with an unnatural amino acid is introduced in a region distant from the TLR5 receptor binding region, including without limitation G212, T213, G238, G239, T240, G241. In some embodiments the substituted amino acid is G239. In some embodiments the unnatural amino acid is homopropargylglycine.

To optimize the substitution of methionine for an unnatural amino acid, it can be desirable to remove methionines naturally present in flagellin, so that the unnatural amino acid is targeted to a single position. In certain embodiments, the native methionine residues close to the TLR5 receptor binding region of flagellin, e.g. M310 and M466, are substituted with a non-polar amino acid other than methionine, e.g. A, G, V, I, L, F, etc.

Where the unnatural amino acid is introduced at residue 1, the protein can be further optimized by substitution of the alanine at residue 2 with a different amino acid, preferably one selected from I, L, N or D. This substitution prevents the cleavage of the N-terminal amino acid by MAP.

In some embodiments, the set of amino acid substitutions, relative to SEQ ID NO:1, is [G239M, M3110I, M466I], as shown in SEQ ID NO:3. In another specific embodiment, the set of substitutions is [A2I or A2L; M3110I, M466I], as shown in SEQ ID NO:7.

Additional substitutions or insertions may be made of 1, 2, 3, 4, 5, or more amino acids, where the substitutions may be conservative or non-conservative, so long as the fast folding and alpha-helical nature of the protein is not changed. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine). Such substitutions or insertions may introduce sequences useful as purification tags, for example the tag WSHPQFEK, which may be fused to the flagellin for ease of purification.

Modifications of interest that do not alter primary sequence include chemical derivatization of polypeptides, e.g., acylation, pegylation, acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The invention further provides nucleic acids encoding the flagellin polypeptides of the invention. As will be appreciated by those in the art, due to the degeneracy of the genetic code, an extremely large number of nucleic acids may be made, all of which encode the flagellin polypeptides of the present invention. Thus, having identified a particular amino acid sequence, those skilled in the art could make any number of different nucleic acids, by simply modifying the sequence of one or more codons in a way that does not change the amino acid sequence.

Using the nucleic acids of the present invention that encode a flagellin polypeptide, a variety of expression constructs can be made. The expression constructs may be self-replicating extrachromosomal vectors or vectors which integrate into a host genome. Alternatively, for purposes of cell-free expression the construct may include those elements required for transcription and translation of the desired polypeptide, but may not include such elements as an origin of replication, selectable marker, etc. Cell-free constructs may be replicated in vitro, e.g. by PCR, and may comprise terminal sequences optimized for amplification reactions.

Generally, expression constructs include transcriptional and translational regulatory nucleic acid operably linked to the nucleic acid encoding the fusion protein. The term "control sequences" refers to DNA sequences necessary for the expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading phase. Linking is accomplished by ligation or through amplification reactions. Synthetic oligonucleotide adaptors or linkers may be used for linking sequences in accordance with conventional practice.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in in vitro expression systems, such as the T7 promoter.

In addition, the expression construct may comprise additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

Cell-Free Synthesis

In some embodiments of the invention, the flagellin polypeptide is produced by cell-free, or in vitro synthesis, in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. A number of reaction chemistries for polypeptide synthesis can be used in the methods of the invention. For example, reaction chemistries are described in U.S. Pat. No. 6,337,191, issued Jan. 8, 2002, and U.S. Pat. No. 6,168,931, issued Jan. 2, 2001, herein incorporated by reference. In some embodiments the reaction conditions are modified to improve formation of disulfide bonds, e.g. as set forth in U.S. Pat. No. 7,871,794, herein specifically incorporated by reference.

In one embodiment of the invention, the reaction chemistry is as described in co-pending U.S. patent application Ser. No. 10/643,683, filed Aug. 18, 2003, herein incorporated by reference. Oxidative phosphorylation is activated, providing for increased yields and enhanced utilization of energy sources. Improved yield is obtained by a combination of factors, including the use of biological extracts derived from bacteria grown on a glucose containing medium; an absence of polyethylene glycol; and optimized magnesium concentration. This provides for a system homeostatic in [$PO_4$] and pH, in which synthesis can occur even in the absence of secondary energy sources.

The template for cell-free protein synthesis can be either mRNA or DNA. Translation of stabilized mRNA or combined transcription and translation converts stored information into protein. The combined system, generally utilized in E. coli systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally added between 50-250 mM and ammonium between 0-100 mM. The pH of the reaction is generally between pH 6 and pH 9. The temperature of the reaction is generally between 20° C. and 40° C. These ranges may be extended.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome of the extract source cells.

Vesicles, either purified from the host organism or synthetic, may also be added to the system. These may be used to enhance protein synthesis and folding. This cytomim technology has been shown to activate processes that utilize membrane vesicles containing respiratory chain components for the activation of oxidative phosphorylation. The present methods may be used for cell-free expression to activate other sets of membrane proteins.

The C-terminal D0 domain of flagellin is susceptible to proteolytic degradation, and in some embodiments the CFPS is performed in the presence of a protease inhibitor cocktail. For example, the reaction mixture comprise one or more of AEBSF, Aprotinin, Bestatin, E-64, Leupeptin and Pepstatin A; and may comprise an effective dose of all of the inhibitors, where an effective dose is that sufficient to prevent flagellin degradation during synthesis. In other embodiments the bacterial cell extract for the CFPS is derived from a bacteria deficient in proteases, for example E. coli BL21, whichis deficient in the Lon and OmpT proteases. The GroEL-GroES (GroEL/S) chaperonin may be overexpressed or exogenously added to the extract for improved yield.

Synthetic systems of interest include the replication of DNA, which may include amplification of the DNA, the transcription of RNA from DNA or RNA templates, the translation of RNA into polypeptides, and the synthesis of complex carbohydrates from simple sugars.

The reactions may be large scale, small scale, or may be multiplexed to perform a plurality of simultaneous syntheses. Additional reagents may be introduced to prolong the period of time for active synthesis. Synthesized product is usually accumulated in the reactor and then is isolated and purified according to the usual methods for protein purification after completion of the system operation.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include E. coli extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salts, polymeric compounds, cyclic AMP, inhibitors for protein or nucleic acid degrading enzymes, inhibitors or regulators of protein synthesis, oxidation/reduction adjusters, non-denaturing surfactants, buffer components, putrescine, spermine, spermidine, etc.

The salts preferably include potassium, magnesium, and ammonium salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol, ascorbic acid, glutathione and/or their oxides. Also, a non-denaturing surfactant such as Triton X-100 may be used at a concentration of 0-0.5 M. Spermine and spermidine or optionally, in combination, putrescine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5-10 and a temperature of 20°-50° C., and more preferably, in the range of pH 6-9 and a temperature of 25°-40° C.

Formulations and Uses

The polypeptides, including particles comprising such polypeptides may be provided in a pharmaceutically acceptable excipient, and may be in various formulations. As is well known in the art, a pharmaceutically acceptable excipient is a relatively inert substance that facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington's Pharmaceutical Sciences 19th Ed. Mack Publishing (1995).

Other formulations include suitable delivery forms known in the art including, but not limited to, carriers such as liposomes. Mahato et al. (1997) Pharm. Res. 14:853-859. Liposomal preparations include, but are not limited to, cytofectins, multilamellar vesicles and unilamellar vesicles.

Generation of a VLP

For the site-specific incorporation of non-natural amino acids (nnAAs) with an alkyne moiety in flagellin, the method of global methionine replacement may be used in the context of CFPS, where methionine is omitted from the reaction mixture, and a methionine analog, for example homopropargylglycine (HPG), is present in the reaction mixture.

The counterpart (reative) amino acid is displayed on the surface of a virus-like particle, particularly by introduction of an unnatural amino acid bearing an azide moiety, for example as disclosed in U.S. Patent application US2010/0168402, herein specifically incorporated by reference. For example, azidohomoalanine (AHA), may be present on the VLP surface. It will be understood by one of skill in the art that the azide/alkyne moieties may be present on either the VLP or the flagellin, so long as each is present on one of the components.

The azide-alkyne cycloaddition reactions are conducted under conditions as known in the art, for example in an anaerobic environment in the presence of tetrakis(acetonitrile)copper(I)hexafluorophosphate catalyst ([(CH$_3$CN)$_4$Cu]PF$_6$ or simply Cu(I) catalyst). The conjugated VLP-flagellin assemblies are optionally purified, e.g. by size exclusion chromatography, sedimentation, etc., and the like as known in the art. The conjugated VLP-flagellin assemblies can then be formulated for administration.

Administration and Assessment of the Immune Response

The flagellin-VLP compositions, or the CFPS-produced flagellin protein of the invention can be administered in combination with other pharmaceutical and/or immunogenic and/or immunostimulatory agents and can be combined with a physiologically acceptable carrier thereof.

As with all immunogenic compositions, the immunologically effective amounts and method of administration of the particular formulation can vary based on the individual, what condition is to be treated and other factors evident to one skilled in the art. Factors to be considered include the antigenicity, whether or not the adjuvant will be complexed with or covalently attached to an immunogen or delivery molecule, route of administration and the number of immunizing doses to be administered. Such factors are known in the art and it is well within the skill of immunologists to make such determinations without undue experimentation. A suitable dosage range is one that provides the desired modulation of immune response to the antigen. Generally, a dosage range of the composition may be, for example, from about any of the following: 0.01 to 100 µg, 0.01 to 50 µg, 0.01 to 25 µg, 0.01 to 10 µg, 1 to 500 µg, 100 to 400 µg, 200 to 300 µg, 1 to 100 µg, 100 to 200 µg, 300 to 400 µg, 400 to 500 µg. Alternatively, the doses can be about any of the following: 0.1 µg, 0.25 µg, 0.5 µg, 1.0 µg, 2.0 µg, 5.0 µg, 10 µg, 25 µg, 50 µg, 75 µg, 100 µg. Accordingly, dose ranges can be those with a lower limit about any of the following: 0.1 µg, 0.25 µg, 0.5 µg and 1.0 µg; and with an upper limit of about any of the following: 250 µg, 500 µg and 1000 µg. In these compositions, the molar ratio of adjuvant to antigen may vary. The absolute amount given to each patient depends on pharmacological properties such as bioavailability, clearance rate and route of administration.

The effective amount and method of administration of the particular linker-antigen formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. The absolute amount given to each patient depends on pharmacological properties such as bioavailability, clearance rate and route of administration.

Parenteral routes of administration include but are not limited to electrical (iontophoresis) or direct injection such as direct injection into a central venous line, intravenous, intramuscular, intraperitoneal, intradermal, or subcutaneous injection. Compositions suitable for parenteral administration include, but are not limited to, pharmaceutically acceptable sterile isotonic solutions. Such solutions include, but are not limited to, saline and phosphate buffered saline for injection of the linker-containing compositions.

Naso-pharyngeal and pulmonary routes of administration include, but are not limited to, inhalation, transbronchial and transalveolar routes. The invention includes linker/antigen-containing compositions suitable for administration by inhalation including, but not limited to, various types of aerosols for inhalation, as well as powder forms for delivery systems. Devices suitable for administration by inhalation of linker/antigen-containing compositions include, but are not limited to, atomizers and vaporizers. Atomizers and vaporizers filled with the powders are among a variety of devices suitable for use in inhalation delivery of powders.

The methods of producing suitable devices for injection, topical application, atomizers and vaporizers are known in the art and will not be described in detail.

The above-mentioned compositions and methods of administration are meant to describe but not limit the methods of administering the linker/antigen-containing compositions of the invention. The methods of producing the various compositions and devices are within the ability of one skilled in the art and are not described in detail here.

Analysis (both qualitative and quantitative) of the immune response to linker/antigen-containing compositions can be by any method known in the art, including, but not limited to, measuring antigen-specific antibody production (including measuring specific antibody subclasses), activation of specific populations of lymphocytes such as CD4+ T cells or NK cells, production of cytokines such as IFNγ, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Serum concentrations of cytokines can be measured, for example, by ELISA.

These and other assays to evaluate the immune response to an immunogen are well known in the art. See, for example, Selected Methods in Cellular Immunology (1980) Mishell and Shiigi, eds., W.H. Freeman and Co.

In some instances, a Th1 or Th2-type response is stimulated, i.e., elicited and/or enhanced. With reference to the invention, stimulating a Th1 or Th2-type immune response can be determined in vitro or ex vivo by measuring cytokine production from cells treated with linker as compared to those treated without linker. Methods to determine the cytokine production of cells include those methods described herein and any known in the art. The type of cytokines produced in response to treatment indicates a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, IL-15, and IFN-γ. In contrast, "Th2-type biased cytokines" refers to those associated with a Th2-type immune response, and include, but are not limited to, IL-4, IL-5, and IL-13. Cells useful for the determination of linker activity include cells of the immune system, primary cells isolated from a host and/or cell lines, usually APCs and lymphocytes.

Methods of the Invention

The invention also includes methods of modulating an immune response comprising administering an immunogenic formulation as described herein to an individual in an amount sufficient to modulate the immune response. Generally, the individual is in need of, or will be in need of, such modulation, due, for example, for a disease condition or being at risk of developing a disease condition. Examples of disease conditions include, but are not limited to, allergy, cancer, infectious diseases (such as viral or bacterial infection).

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Ordered flagellin array as an immunostimulant. Immunestimulation by bacterial flagellins has been explored as a potential vaccine adjuvant both for induction of specific humoral and cellular immune responses. Flagellin monomers (FIG. 1) have four globular domains (D0, D1, D2 and D3), of which the D0 and D1 domains are the most highly conserved. Recent studies suggest that the conserved D1 and D2 domains are important for innate immune system stimulation.

Figure 2:
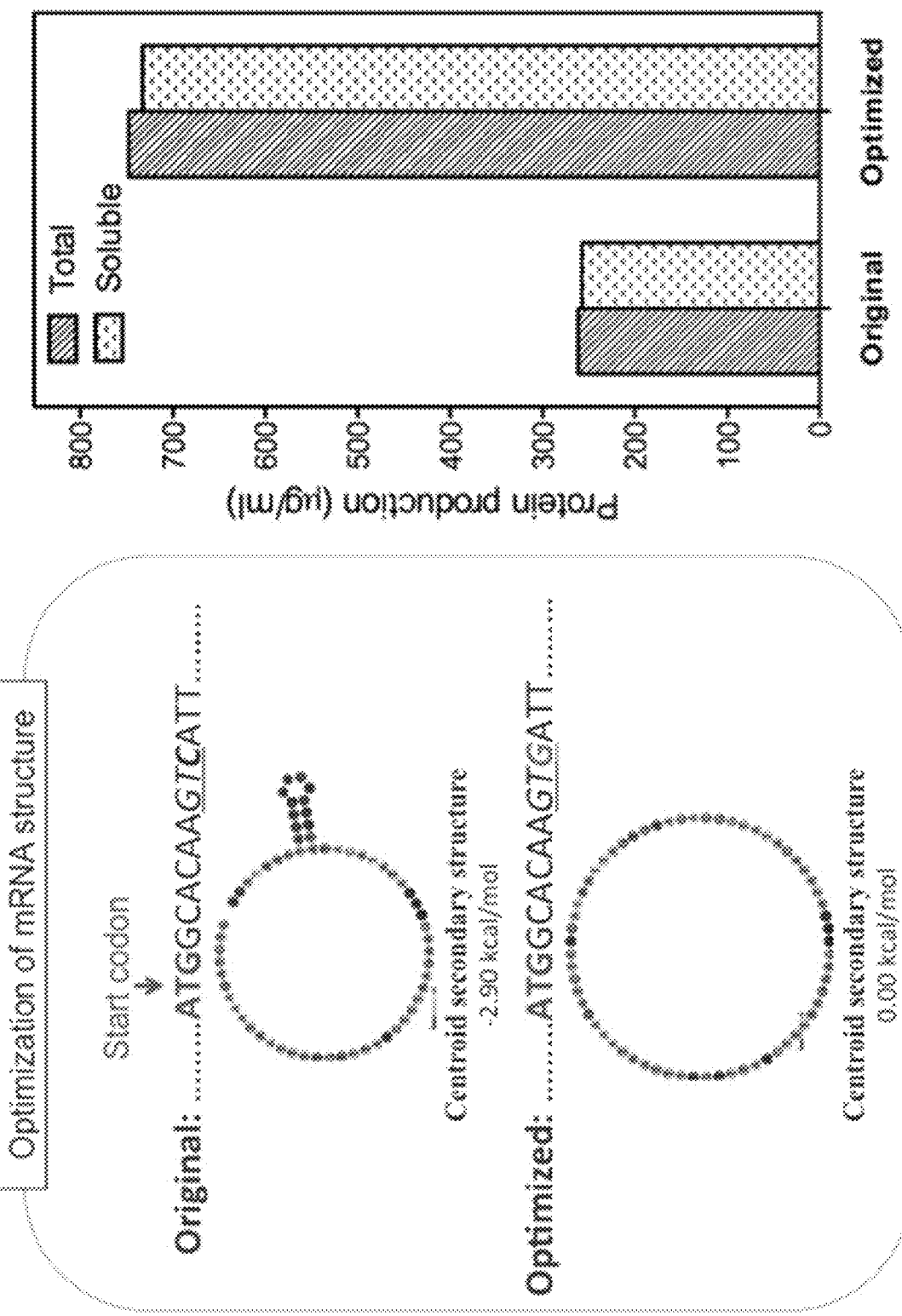
FIG. 2 Increase of protein yield by optimizing mRNA structure.

Cell-free protein synthesis (CFPS) provides a means for rapid production of flagellin protein. We cloned the flagellin gene (flic) from *Salmonella typhimurium* SL1344. The protein yield was 260 μg/ml. To increase the yield, we optimized the mRNA secondary structure of the first 40 nucleotides. By the mutation of only one nucleotide, the protein yield increased to 750 μg/ml, as shown in FIG. 2.

Figure 3:
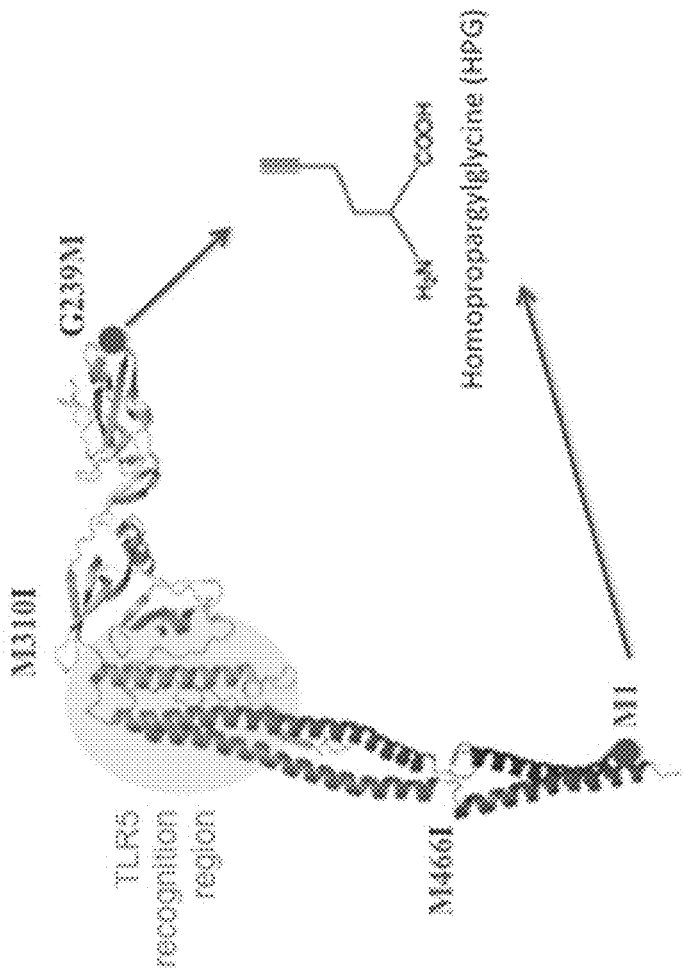
FIG. 3 Methionine mutation design of flagellin.

Virus-like particles (VLPs) can elicit strong immune response. We sought to attach flagellin protein to VLPs in order to present them in the optimal orientation for TLR5 stimulation and to present multiple copies of flagellin on each VLP for further improved stimulation. In order to create VLP-flagellin conjugates, we adopted a strategy for replacement of the methionine residues in flagellin with homopropargylglycine (HPG). As shown in FIG. 3, two methionines (M310 and M466) close to the TLR5 receptor binding region were mutated to isoleucine. A glycine far away from TLR5 receptor binding region was mutated to methionine.

Figure 4:
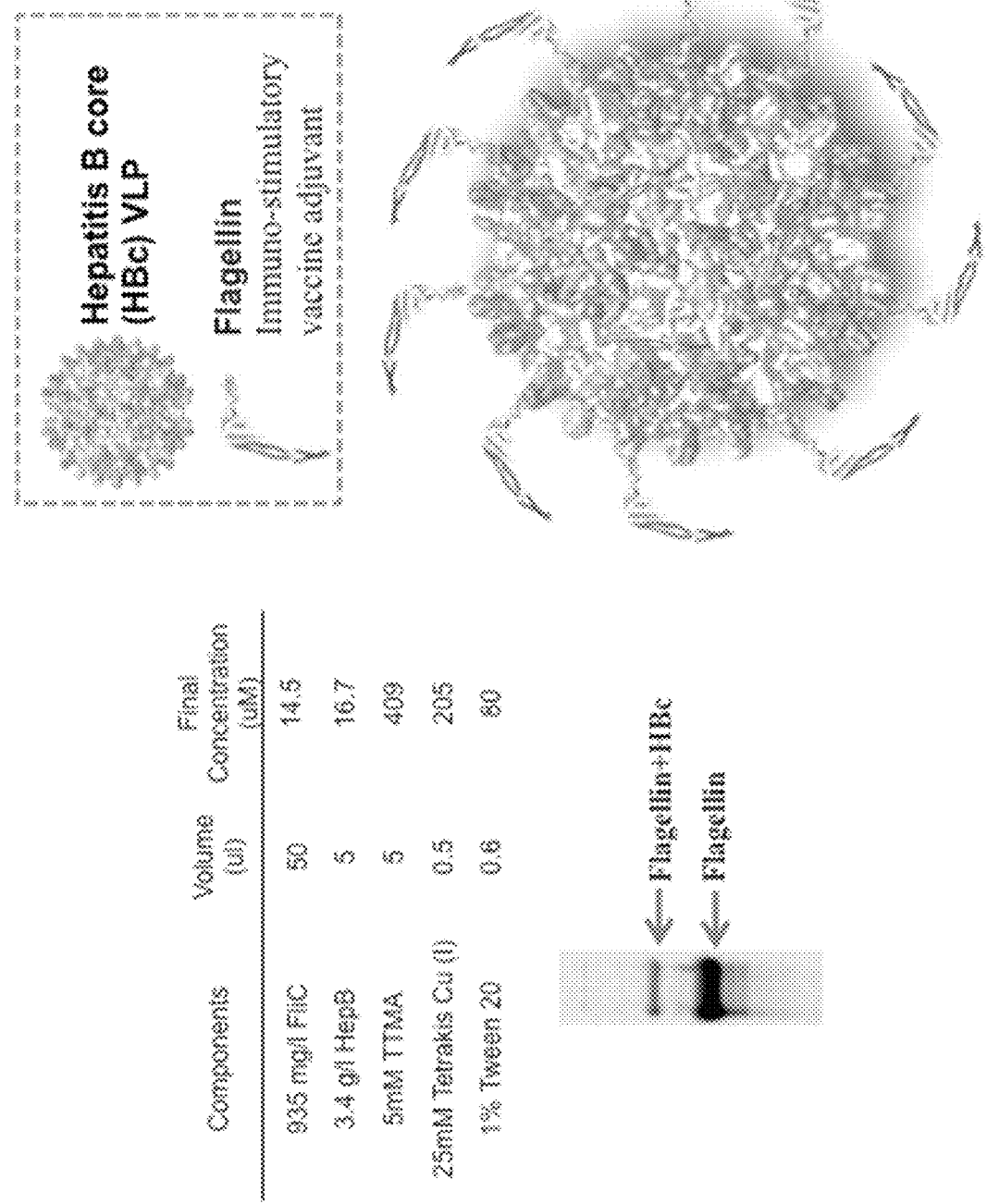
FIG. 4 Conjugation of flagellin to HBc VLP.

In the CFPS system, methionine was replaced with its analog non-natural amino acid homopropargylglycine (HPG). Then HPG with its alkyne group was incorporated into the flagellin protein. We also synthesized the VLPs with an azide group on the VLP surfaces. Using the click azide/alkyne reaction, flagellin was attached to the VLPs, as shown in FIG. 4. Approximately 20 flagellin proteins were attached to one Hepatitis B core (HBc) VLP (240 HBc monomer) as judged using radioactively labeled flagellin. The concentrations of each reagent in the conjugation reaction are indicated in the table and the autoradiogram allows visualization of the HepBcore-flagellin conjugate.

Flagellin bioactivity was further analyzed using HEK-BLUE™-hTLR5 (HEK 293 engineered cell lines), which were purchased and had been produced by co-transfection of the human TLR5 gene and an inducible SEAP (secreted embryonic alkaline phosphatase) reporter gene into HEK293 cells. The SEAP gene is placed under the control of the IFN-β minimal promoter fused to five NF-κB and AP-1-binding sites. Stimulation with a TLR5 ligand activates NF-κB and AP-1 which induce the production of SEAP. Levels of SEAP can be easily determined with QUANTI-BLUE™, a detection molecule that turns purple/blue from pink in the presence of alkaline phosphatase.

The analysis results of flagellin bioactivity (FIG. 5) showed that incorporation of HPG into flagellin did not affect the bioactivity of flagellin. Flagellin attached to the VLPs had approximately 10-fold more activity than free flagellin indicating its superior stimulation of the TLR5 receptor.

Materials and Methods

Construction of plasmids. The flagellin gene (flic) from *Salmonella typhimurium* SL1344 was cloned into the pY71 vector using NdeI and SalI restriction sites. pY71 is a reduced size plasmid (1.76 kb) that utilizes the T7 promoter and contains a pUC19 origin of replication and a kanamycin resistance element (Kuchenreuther et al., 2009). The Strep-tag II purification tag was added at the C-terminus of flagellin. The amino sequence of the constructs containing flagellin and a C-terminal Strep-tag II purification tag are provided as SEQ ID NO:3 and 4.

The 5' end of the construct was further modified using M-fold to reduce formation of secondary structure near the ribosome binding site (Zuker, 2003). The first 15 nucleotides of the modified coding sequence were as follows: ATGGCA-CAAGTGATT, where the changed residue is underlined.

Cell-Free Protein Synthesis (CFPS). CFPS was conducted using the PANOx-SP (PEP, amino acids, nicotinamide adenine dinucleotide (NAD), oxalic acid, spermidine, and putrescine) cell-free system as described previously (Jewett and Swartz 2004) with several modifications. The standard PANOx-SP CFPS reaction mixture includes: 1.2 mM ATP, 0.85 mM each of GTP, UTP, and CTP, 33 mM phosphoenol pyruvate (Roche Molecular Biochemicals, Indianapolis, Ind.), 170 mM potassium glutamate, 10 mM ammonium glutamate, 16 mM magnesium glutamate, 1.5 mM spermidine, 1.0 mM putrescine, 0.17 mg/mL folinic acid, 13.3 µg/mL plasmid, approximately 100-300 µg/mL T7 RNA polymerase, 2 mM of each of the 20 unlabeled amino acids, 0.33 mM NAD, 0.26 mM Coenzyme A (CoA), 2.7 mM potassium oxalate, and 0.28 volumes of *E. coli* KC6 S30 extract (Goerke and Swartz 2008; Knapp et al. 2007). All reagents were obtained from Sigma-Aldrich (St. Louis, Mo.) unless otherwise noted.

CFPS reactions to produce the flagellin protein were conducted at 30° C. for 6 h. Small-scale CFPS reactions were carried out in 20 µL volumes in 1.5 mL microcentrifuge tubes. Preparative-scale reactions used 3 mL volumes with 1 mL per well in 6-well tissue culture plates (BD Falcon #3046, BD, Franklin Lakes, N.J.). 8.4 µM L-[U-$^{14}$C]-Leucine (Perkin Elmer, Waltham, Mass.) was added to small-scale reactions and to 30 µL aliquots of preparative-scale reactions for measuring protein yields using a previously described trichloroacetic acid protocol (Calhoun and Swartz 2005) and a Beckman LS3801 liquid scintillation counter (Beckman Coulter, Fullerton, Calif.). The soluble fraction of preparative-scale reactions was recovered by centrifugation at 21,000×g, 15 min for further evaluation and purification.

Purification of Flagellin Proteins. Soluble CFPS products from 3 mL reactions were purified using the Strep-tag II/Strep-tactin system (IBA Gmbh, Gottingen, Germany). The CFPS reaction product supernatants were then applied to a 1.0 mL Strep-Tactin gravity flow column (IBA Gmbh) and washed with 10 column volume of PBS buffer. The loaded column was eluted with PBS buffer containing 5.0 mM desthiobiotin, and 0.5 mL fractions were analyzed for protein content using SDS PAGE gels. Pooled fractions were then dialyzed in PBS buffer and stored at 4° C.

Constructs used for the assembly of flagellin and virus-like particle (VLP). To introduce sites for the incorporation of non-natural amino acids (nnAAs) with an alkyne group in flagellin, an ATG codon was introduced to replace the previous codon that encodes residue G239 using QuikChange PCR (Stratagene, La Jolla, Calif.). M310 and M466 were also replaced with isoleucine residues to avoid nnAAs introduction at these two sites.

To incorporate nnAA with an azide group in Hepatitis B core (HBc) VLP, a methionine site was introduced at residue 76 for nnAA incorporation using QuikChange PCR. M66 was also replaced with a serine residue to avoid nnAA introduction at this site.

To facilitate nnAAs incorporation into flagellin and HBc antigen respectively, 4 mM of homopropargylglycine (HPG) with an alkyne group (Chiralix B.V., Nijmegen, The Netherlands) and 6 mM of azidohomoalanine (AHA) with an azide group (MedChem Source LLP, Federal Way, Wash.) were added to CFPS reactions respectively. HPG and AHA are analogs of methionine. For global replacement of methionines, methionine was omitted from the CFPS reaction mixtures.

Azide-Alkyne click chemistry. The (3+2) cycloaddition click reactions were conducted in an anaerobic glovebox (Coy Laboratories, Grass Lake, Mich.) to preserve the reduced state of the tetrakis(acetonitrile)copper(I)hexafluorophosphate catalyst ([(CH3CN)4Cu]PF6 or simply Cu(I) catalyst) (Sigma Aldrich, St. Louis, Mo.). Cu(I) catalyst was added to reactions at 1 mM in addition to 0.5 mM of the enhancer ligand, tris(triazolylmethyl) amine (TTMA) (obtained from the Professor Christopher Chidsey Laboratory at Stanford University, Stanford, Calif.), to improve the rate of the click reactions. HBc VLP and flagellin were mixed with the Cu (I) catalyst and TTMA enhancer in 10 mM potassium phosphate (pH 8.0) with 0.01% Tween 20. Before addition of the Cu(I) catalyst, click reaction components were deoxygenated in 1.5 mL microcentrifuge tubes for 1 h in the anaerobic glovebox. The click reactions for attaching HBc VLP to flagellin were conducted for 2 h.

Size Exclusion HPLC. Conjugated HBc VLP-flagellin assemblies were analyzed using a Discovery Bio GFC 150 HPLC column, 15 cm×4.6 mm inner diameter with 5 µM particles (Sigma-Aldrich). The running buffer was 10 mM Tris-HCl pH 7.5, 500 mM sodium chloride, 0.01% Tween 20, pumped at 0.2 mL/min. The sample injection volume was 80 µL. Protein absorbance was monitored in-line at 280 nm over a period of 35 min.

Flagellin bioactivity assay. Flagellin bioactivity was analyzed using HEK-Blue™-hTLR5 cells (Invivogen), which had been generated by co-transfection of the human TLR5 gene and an inducible SEAP (secreted embryonic alkaline phosphatase) reporter gene into HEK293 cells. The SEAP gene was placed under the control of the IFN-β minimal promoter fused to five NF-κB and AP-1-binding sites. Stimulation with a TLR5 ligand activates NF-κB and AP-1 which induce the production of SEAP. Levels of SEAP can be easily determined with QUANTI-Blue™ (Invivogen), a detection medium that turns purple/blue from pink in the presence of alkaline phosphatase.

First a cell suspension of fresh HEK-BLUE™-hTLR5 Cells was prepared at ~140,000 cells per ml in medium which contains 10% (v/v) heat inactivated FBS. Then 20 µl of the flagellin sample was mixed with 180 µl of cell suspension (~25,000 cells) per well of a sterile flat-bottom 96-well plate, and the plate was incubated at 37° C. in a $CO_2$ incubator for 24 h. After 24 h, 20 µl of induced HEK-BLUE™-hTLR5 cell supernatant was mixed with 180 µl of resuspended QUANTI-BLUE™ per well of a flat-bottom 96-well plate and incubated at 37° C. for 1 h. The SEAP levels were determined using a spectrophotometer at 620 nm.

Example 2

Figure 6:
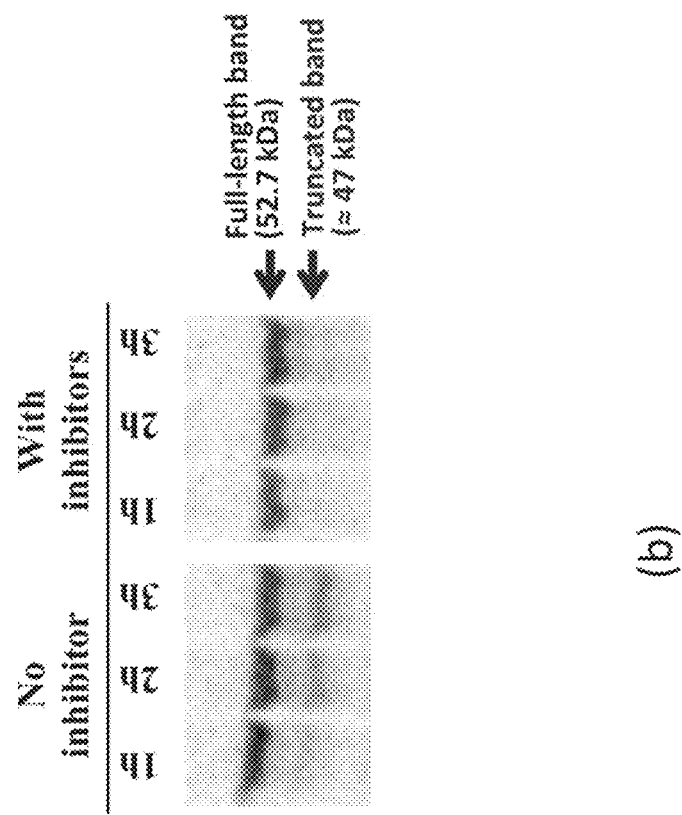
FIG. 6 Effects of protease inhibitor additions on the cell-free protein synthesis and stability of flagellin. (a) Time-course profile of cell-free production of flagellin with and without the protease inhibitor cocktail. (b) SDS-PAGE autoradiogram analysis of flagellin proteins synthesized without and with the protease inhibitor cocktail. KC6 extract was used in the CFPS system.
Figure 6:
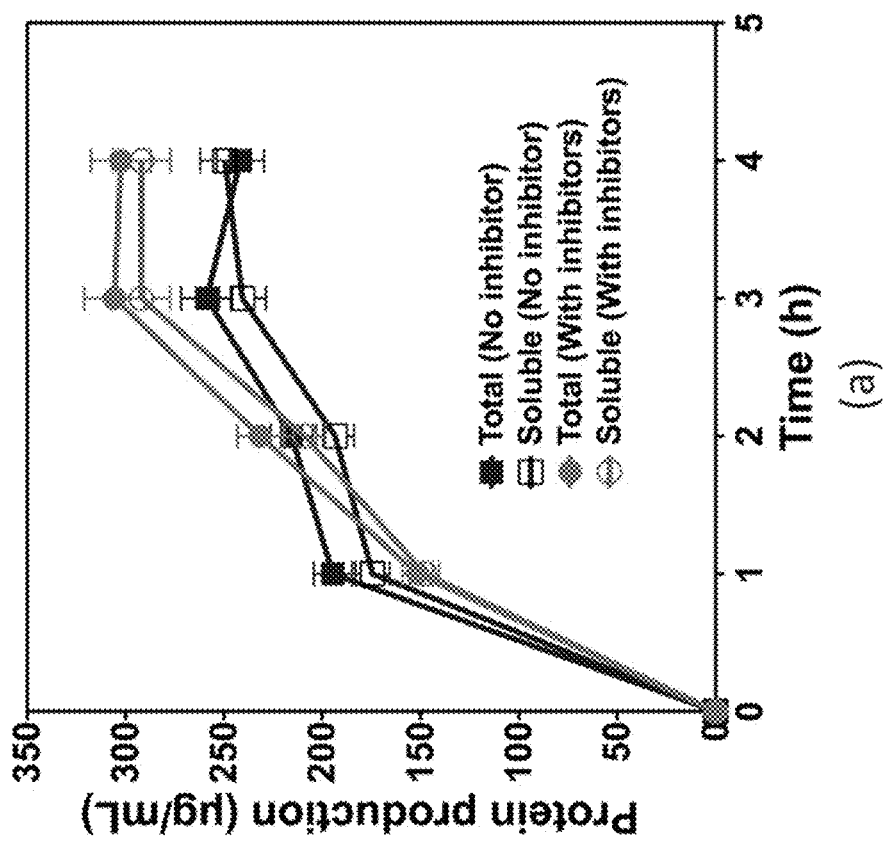

Bacterial flagellin has been explored as a potential vaccine adjuvant for inducing innate immunity. We recently developed an *Escherichia coli*-based cell-free protein synthesis (CFPS) method to rapidly produce soluble flagellin protein. Observations from protein purification and SDS-PAGE indicated that the C-terminal D0 domain of flagellin is susceptible to proteolytic degradation. This proteolysis could be reduced by protease inhibitors. The addition of the protease inhibitor cocktail both increased the yield of flagellin (FIG. 6(a)) and avoided the appearance of the truncated product (FIG. 6(b)).

Figure 7:
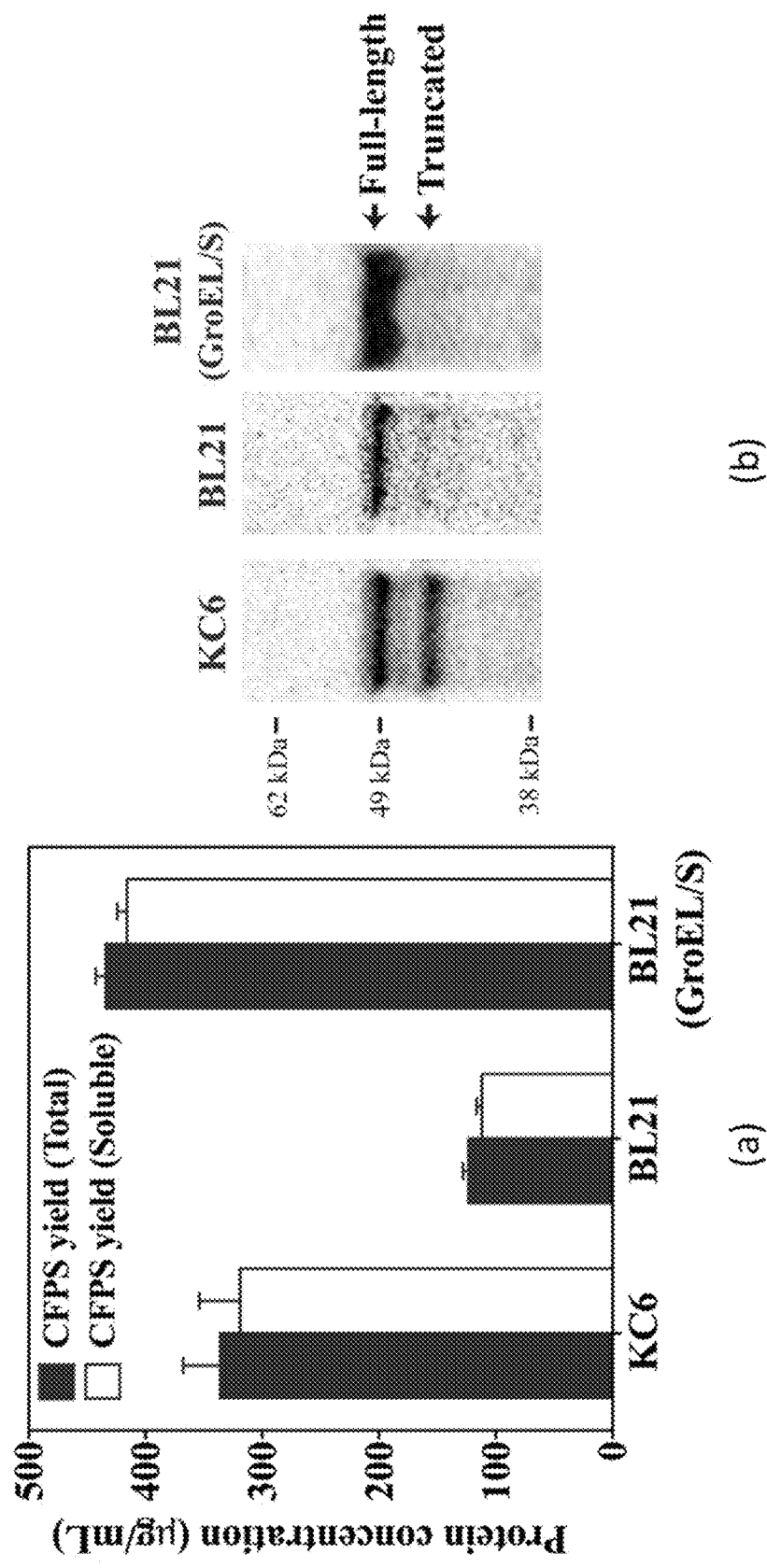
FIG. 7 Effects of different cell extracts on the cell-free protein synthesis and stability of flagellin. (a) Cell-free production of flagellin using 3 different cell extracts (KC6, BL21 and BL21 with GroEL/S chaperonin). (b) SDS-PAGE autoradiogram analysis of flagellin proteins synthesized in the CFPS system.
Figure 8:
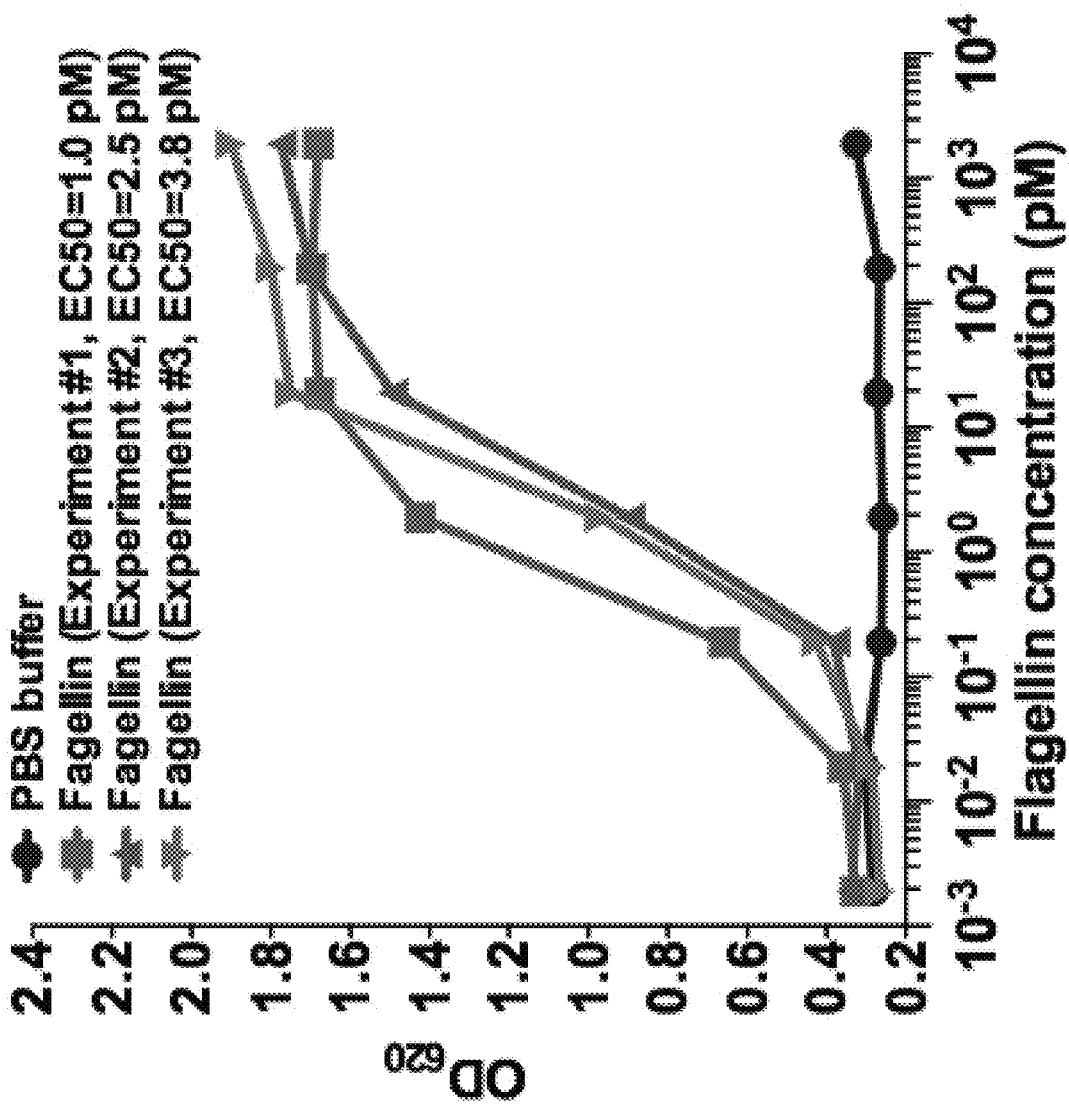
FIG. 8 Bioactivity analysis of purified flagellin protein produced in the CFPS system. Three measurements were taken on different days. PBS buffer was used as the negative control.

Since *E. coli* BL21 is deficient in the Lon and OmpT proteases, we compared BL21 cell extract with KC6 extract in the CFPS system, as shown in FIG. 7. Autoradiography indicated no truncated flagellin accumulation using BL21 extract. However, the total yield using BL21 extract (123.5 µg/mL) was much lower than that using KC6 extract (336.3 µg/mL). To increase the CFPS yield using BL21 extract, the GroEL-GroES (GroEL/S) chaperonin was overexpressed in BL21 cells before preparing the extract (Yang et al. 2011). The addition of GroEL/S increased the yield by 4 fold, and no truncated flagellin accumulated. The product had 8 to 800 fold higher affinity for the TLR5 receptor (EC50=2.4±1.4 pM) (FIG. 3) than previously reported (20 pM to 2 nM, see for example Andersen-Nissen et al. (2005) PNAS 102(26):9247-52; McDermott et al. (2000) Infection and Immunity 68(10): 5525-9; Mizel et al. (2003) JBC 278(26):23624-23629; Saha et al. (2007) J. Immunol. 179(2):1147-54; Skountzou et al. (2010) Vaccine 28(24):4103-12).

We hypothesized that the TLR5 receptor activation could be enhanced if flagellin were presented in an ordered array on the surface of a VLP. CFPS can provide a facile means for introducing non-natural amino acids (nnAAs) with an alkyne moiety into flagellins and nnAAs with an azide moiety into VLPs. This then enables the direct coupling of flagellin to VLPs using Cu(I)-catalyzed azide-alkyne cycloaddition reaction (Patel and Swartz (2011) Bioconjugate Chemistry 22(3): 376-387; Welsh et al. (2009) Biochemical and Biophysical Research Communications 389(4):563-568). In order to create a VLP-Flagellin conjugate, we adopted a strategy for replacement of the methionine residues in flagellin with homopropargylglycine (HPG).

Figure 5:
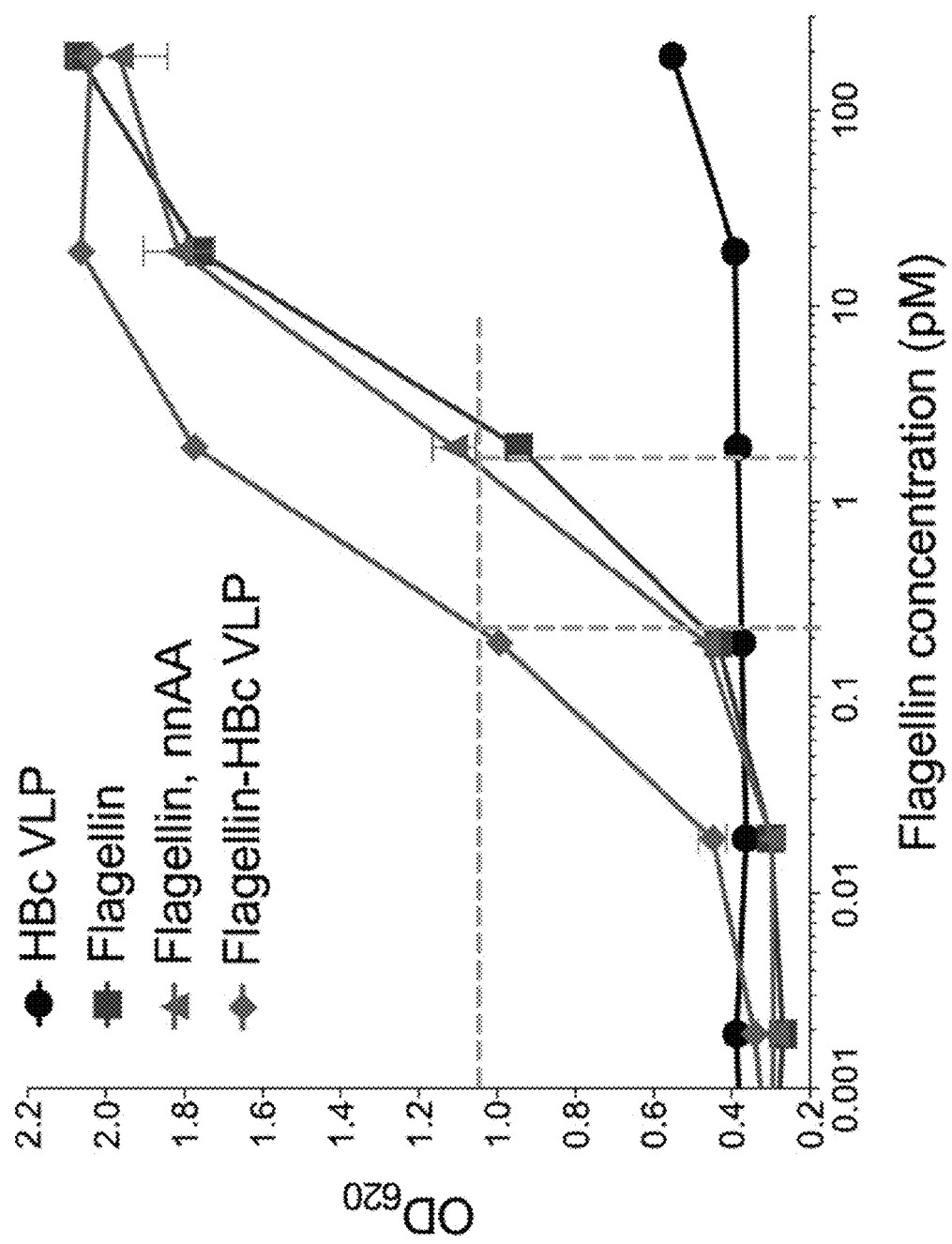
FIG. 5 Flagellin bioactivity assay.

In order to present the TLR5 recognition region on the external surface of the VLP, we reasoned that optimal attachment geometry would result if the nnAA HPG with an alkyne moiety was inserted either near the N-terminus of flagellin or at the distal end of the D3 domain. We previously studied the Gly239 site (at the distal end of the D3 domain) as the nnAA site. Two methionines (M310 and M466) close to the TLR5 receptor binding region were mutated to isoleucine to avoid the incorporation of HPG at these sites (FIG. 3). We also can synthesize the VLPs with an azide group. Using the click azide/alkyne reaction, around 20 flagellin proteins were attached to one Hepatitis B core (HBc) VLP (240 HBc monomers). The ordered and oriented VLP display of flagellin increased its specific TLR5 stimulation activity by approximately 10-fold (FIG. 5).

The nnAA site at Met1 (N-terminus) was also evaluated. In *E. coli*, an enzyme called methionine aminopeptidase (MAP) performs the post-translational N-terminal methionine excision from nascent polypeptides during protein synthesis (Benbassat et al. (1987) Journal of Bacteriology 169(2):751-757; Narayanan and Nampoothiri (2012) Molecular and Cellular Biochemistry 365(1-2):191-202). The excision is heavily dependent on the amino acid in the second position. The cleavage of the N-terminal Met by MAP is most efficient if the amino acid in the second (P') position is Ala, Gly or Ser (Frottin et al. (2006) Molecular & Cellular Proteomics 5(12): 2336-2349). In particular, the N-terminal methionine could not be cleaved by MAP if peptides had Ile, Asn, Asp, Met, or Leu at the second (P') position (Frottin et al. 2006).

Figure 9:
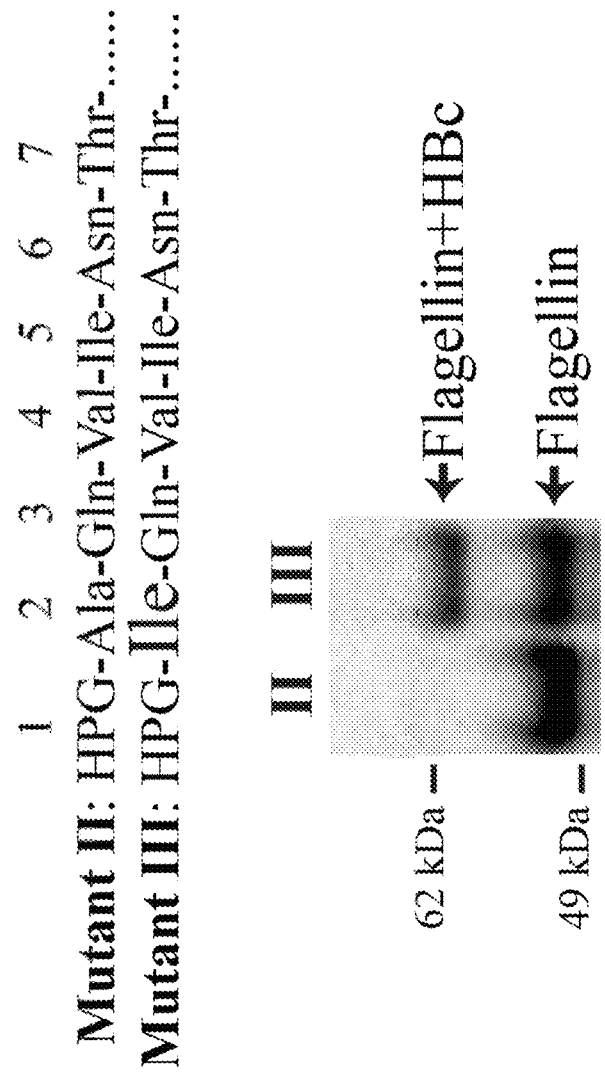
FIG. 9 Attachment of flagellins to HBc VLPs. Mutation II: M1HPG, M310I and M466I. Mutation III: M1HPG, Ala2Ile, M310I and M466I.
Figure 10:
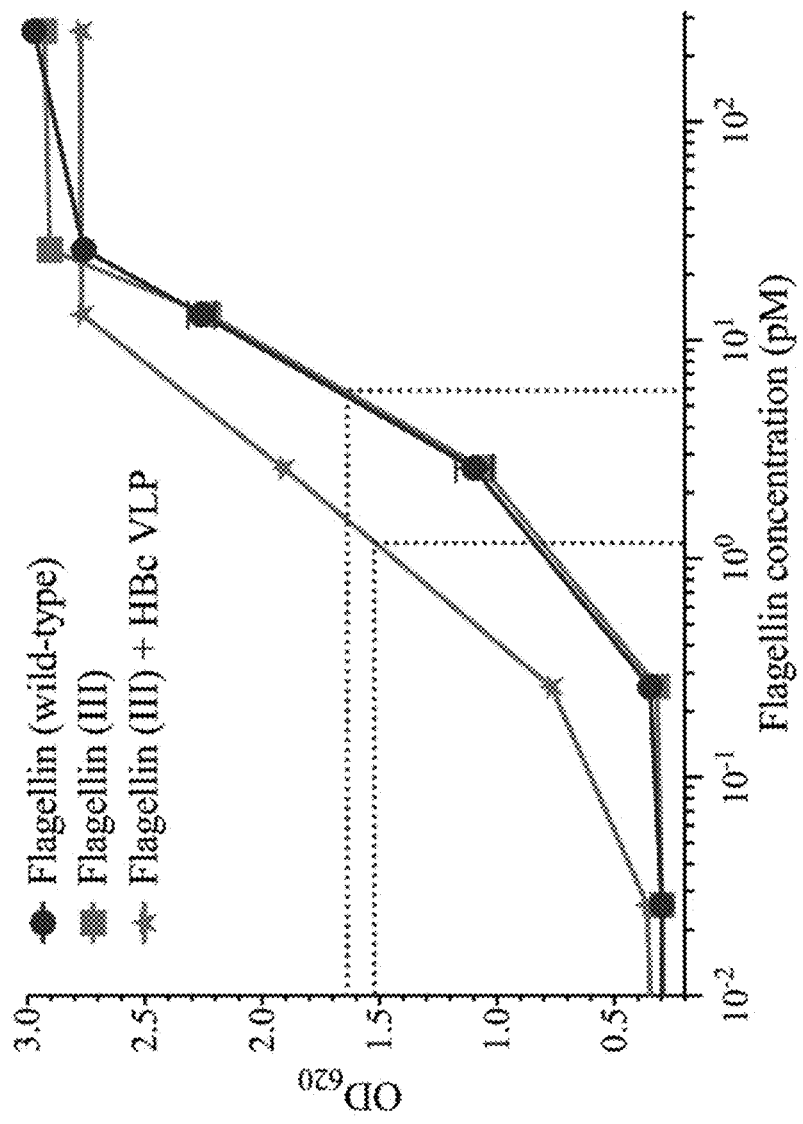
FIG. 10. Bioactivity assay of conjugates of flagellin and HBc VLP. Note that 6 pM affinity is indicated for flagellin in this experiment. This reflects normal variation for the bioassay.

The second amino acid in the wild-type flagellin is Ala. If the nnAA methionine anologue HPG was incorporated into the Met1 site, it could be removed by MAP. To inhibit the cleavage, the second amino acid Ala was mutated to Ile (A2Imutation). The click-reaction results showed that the mutation, Ala2Ile, successfully avoided the removal of the N-terminal nnAA HPG (FIG. 9) as indicated by the failure of the conjugation reaction for mutant II and successful conjugation of mutant III. Gel densitometry estimated that around 50 flagellin proteins could be attached to 1 HBc VLP (240 monomers). The bioactivity assay indicated that the VLP-conjugated flagellin is approximately 5-fold more active than free flagellin in stimulating the TLR5 receptor (FIG. 10).

Materials and Methods

Sequence of different variants. The sequences of different variants are provided in the sequence listing as follows:

| Variants | Protein sequence | DNA encoding sequence |
|---|---|---|
| Wild-type | SEQ ID NO: 1 | SEQ ID NO: 2 |
| II | SEQ ID NO: 5 | SEQ ID NO: 6 |
| III | SEQ ID NO: 7 | SEQ ID NO: 8 |

Cell-Free Protein Synthesis (CFPS). CFPS was conducted using the PANOx-SP (PEP, amino acids, nicotinamide adenine dinucleotide (NAD), oxalic acid, spermidine, and putrescine) cell-free system as described previously (Jewett and Swartz (2004) Biotechnology and Bioengineering 86(1): 19-26) with several modifications. The standard PANOx-SP CFPS reaction mixture includes: 1.2 mM ATP, 0.85 mM each of GTP, UTP, and CTP, 33 mM phosphoenol pyruvate (Roche Molecular Biochemicals, Indianapolis, Ind.), 170 mM potassium glutamate, 10 mM ammonium glutamate, 16 mM magnesium glutamate, 1.5 mM spermidine, 1.0 mM putrescine, 0.17 mg/mL folinic acid, 13.3 µg/mL plasmid, approximately 100-300 µg/mL T7 RNA polymerase, 2 mM of each of the 20 unlabeled amino acids, 0.33 mM NAD, 0.26 mM Coenzyme A (CoA), 2.7 mM potassium oxalate, and 0.28 volumes of *E. coli* KC6 extract (Goerke and Swartz 2008), BL21 extract or BL21(GroE/S) extract. For protease inhibitor studies, 2 g/l of Protease Inhibitor Cocktail (including AEBSF, Aprotinin, Bestatin, E-64, Leupeptin and Pepstatin A) was added in CFPS reactions. All reagents were obtained from Sigma-Aldrich (St. Louis, Mo.) unless otherwise noted.

CFPS reactions to produce the flagellin protein were conducted at 30° C. for 6 h. Small-scale CFPS reactions were carried out in 20 µL volumes in 1.5 mL microcentrifuge tubes. Preparative-scale reactions used 3 mL volumes with 1 mL per well in 6-well tissue culture plates (BD, Franklin Lakes, N.J.). 8.4 µM L-[U-$^{14}$C]-Leucine (PerkinElmer, Waltham, Mass.) was added to small-scale reactions and to 30 µL aliquots of preparative-scale reactions for measuring protein yields using a previously described trichloroacetic acid protein precipitation protocol (Calhoun and Swartz (2005) Biotechnology Progress 21(4):1146-1153) and a Beckman L53801 liquid scintillation counter (Beckman Coulter, Fullerton, Calif.). The soluble fraction of preparative-scale reactions was recovered by centrifugation at 21,000×g for 15 min for further evaluation and purification.

Protein size was analyzed by SDS-PAGE gel and autoradiography. NuPAGE Novex precast gels and reagents were purchased from Invitrogen (Carlsbad, Calif.). For reducing SDS-PAGE, samples were denatured for 10 min at 95° C. in loading buffer (1×LDS running buffer and 50 mM dithiothreitol). For non-reducing SDS-PAGE, samples were only mixed with LDS running buffer without addition of dithiothreitol and heat treatment. The samples were loaded onto a 10% (w/v) Bis-Tris precast gel using the SeeBlue Plus2 molecular weight standard, and the electrophoresis was conducted using the MES running buffer (Invitrogen). SimplyBlue SafeStain (Invitrogen) was used to stain and fix the gels according to the manufacturer's recommendations. The gels were dried using a gel dryer model 583 (Bio-Rad, Richmond, Calif.), before exposure to storage phosphor screen (Molecular Dynamics), which was subsequently scanned using a Typhoon Scanner (GE Healthcare). ImageJ software was used to compare the density of bands on the gel to determine the yield of full-length protein.

Purification of Flagellin Proteins. Soluble CFPS products from 3 mL reactions were purified using Strep-tag II/Strep-tactin affinity chromatography (IBA Gmbh, Gottingen, Germany). The soluble fractions of the CFPS solution were applied to a 1.0 mL Strep-Tactin gravity flow column (IBA Gmbh) and washed with 10 mL of PBS buffer (pH 7.4). The loaded column was eluted with PBS buffer containing 5.0 mM desthiobiotin, and 0.5 mL fractions were analyzed for protein content using SDS PAGE gels. Pooled fractions were then dialyzed against PBS buffer to remove the desthiobiotin and stored at 4° C.

Constructs used to produce flagellin for conjugation to virus-like particles (VLPs). For the site-specific incorporation of non-natural amino acids (nnAAs) with an alkyne moiety in flagellin, the method of global methionine replacement was used. An ATG codon was introduced to replace the previous codon that encodes residue G239 using QuikChange PCR. M310 and M466 were replaced with isoleucine residues to avoid nnAAs introduction at these two sites by changing the codon ATG to ATC. Four mM of the methionine analogue homopropargylglycine (HPG) (Chiralix B.V., Nijmegen, The Netherlands) with an alkyne moiety was added to CFPS reactions. For these reactions, methionine was omitted from the CFPS reaction mixtures.

To display an azide moiety on the surface of Hepatitis B core antigen (HBc) VLPs, a methionine codon (ATG) was introduced using QuikChange PCR to encode residue 76 for nnAA incorporation. The M66 codon was replaced with a serine codon (AGC) to avoid nnAA introduction at this site. Six mM of methionine analogue azidohomoalanine (AHA) (MedChem Source LLP, Federal Way, Wash.) with an azide moiety was added to CFPS reactions. Methionine was also omitted from these CFPS reaction mixtures.

Azide-Alkyne cycloaddition and purification. The azide-alkyne cycloaddition reactions were conducted in an anaerobic glovebox (Coy Laboratories, Grass Lake, Mich.) to preserve the reduced state of the tetrakis(acetonitrile)copper(I) hexafluorophosphate catalyst ($[(CH_3CN)_4Cu]PF_6$ or simply Cu(I) catalyst) (Sigma Aldrich, St. Louis, Mo.). Cu(I) catalyst was added to reactions at 1 mM. HBc VLP and flagellin were mixed with the Cu (I) catalyst in 20 mM potassium phosphate (pH 8.0) with 0.01% Tween 20. Before addition of the Cu(I) catalyst, click reaction components were deoxygenated in 1.5 mL microcentrifuge tubes for 1 h in the anaerobic glovebox. The click reactions for attaching HBc VLP to flagellin were conducted for 2 h.

Conjugated HBc VLP-flagellin assemblies were then analyzed and purified by size exclusion chromatography using an Ultrahydrogel 500 HPLC column (30 cm×7.8 mm inner diameter with 10 μM particles) (Waters). The running buffer was PBS (pH 7.4) buffer, pumped at 0.3 mL/min. The injection volume was 90 μL. Protein absorbance was monitored in-line at 280 nm over a period of 60 min.

Flagellin bioactivity assay. Flagellin bioactivity was analyzed using HEK-BLUE™-hTLR5 cells (Invivogen), which had been generated by co-transfection of the human TLR5 gene and an inducible SEAP reporter gene into HEK293 cells. Firstly, a cell suspension of fresh HEK-BLUE™-hTLR5 Cells was prepared at ~140,000 cells per ml in medium containing 10% (v/v) heat-inactivated FBS. Then, 20 μL of the flagellin sample was mixed with 180 μl of cell suspension (~25,000 cells) per well in a sterile flat-bottom 96-well plate, and the plate was incubated at 37° C. in a $CO_2$ incubator for 24 h. After that, 20 μL of induced HEK-BLUE™-hTLR5 cell supernatant was mixed with 180 μL of resuspended QUANTI-BLUE™ per well of a flat-bottom 96-well plate and incubated at 37° C. for 1 h. The relative SEAP concentrations were determined by absorbance at 620 nm using a VersaMax microplate reader.

What is claimed is:

1. An adjuvant formulation comprising: an ordered array comprising: flagellin protein covalently linked through an unnatural amino acid to a virus-like particle (VLP) wherein the flagellin protein is modified to: (a) comprise the unnatural amino acid at a site corresponding to M1 of SEQ ID NO:1, wherein the unnatural amino acid is selected from homopropargylglycine (HPG), p-acetyl-L-phenylalanine, p-propargyloxyphenylalanine, and p-azido-L-phenylalanine; and (b) methionine residues corresponding to M310 and M466 of SEQ ID NO:1 are substituted with a non-polar amino acid other than methionine; and a pharmaceutically acceptable excipient.

2. The adjuvant formulation of claim 1, wherein the flagellin protein comprises SEQ ID NO:7.

3. A flagellin protein modified to comprise (a) an unnatural amino acid selected from homopropargylglycine (HPG), p-acetyl-L-phenylalanine, p-propargyloxyphenylalanine, and p-azido-L-phenylalanine at a site corresponding to amino acid residue M1, of SEQ ID NO:1; and (b) methionine residues corresponding to M310 and M466 of SEQ ID NO:1 are substituted with a non-polar amino acid other than methionine.

4. The flagellin protein of claim 3, wherein the protein comprises a single unnatural amino acid.

5. The flagellin protein of claim 3, wherein the unnatural amino acid is homopropargylglycine (HPG).

6. A flagellin protein comprising a homopropargylglycine or methionine at the amino acid position corresponding to G239 of SEQ ID NO:1.

7. The flagellin protein of claim 6, wherein the methionine residues corresponding to M310 and M466 of SEQ ID NO:1 are substituted with a non-polar amino acid other than methionine.

8. The flagellin protein of claim 6, having the amino acid sequence of SEQ ID NO:3.

9. A flagellin protein modified to comprise
   (a) homopropargylglycine (HPG) at the amino acid residue corresponding to M1 of SEQ ID NO:1
   (b) an amino acid substitution selected from A2I or A2L; and
   (c) methionine residues corresponding to M310 and M466 of SEQ ID NO:1 are substituted with a non-polar amino acid other than methionine.

10. A flagellin protein having the amino acid sequence of SEQ ID NO:7.

* * * * *

SEQUENCE LISTING

```
<160> NUMBER OF SEQ ID NOS: 8

<210> SEQ ID NO 1
<211> LENGTH: 503
<212> TYPE: PRT
<213> ORGANISM: Salmonella typhimurium
<220> FEATURE:
<221> NAME/KEY: PEPTIDE
<222> LOCATION: (496)...(503)
<223> OTHER INFORMATION: Strep-tag II polypeptide

<400> SEQUENCE: 1

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60
```

```
Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Trp
```

Ser His Pro Gln Phe Glu Lys
        500

<210> SEQ ID NO 2
<211> LENGTH: 1512
<212> TYPE: DNA
<213> ORGANISM: Salmonella typhimurium

<400> SEQUENCE: 2

```
atggcacaag tgattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggtgcc aacgacggtg aaactatcga tatcgatctg     480
aagcagatca actctcagac cctgggtctg gatacgctga atgtgcaaca aaaatataag     540
gtcagcgata cggctgcaac tgttacagga tatgccgata ctacgattgc tttagacaat     600
agtactttta aagcctcggc tactggtctt ggtggtactg accagaaaat tgatggcgat     660
ttaaaatttg atgatacgac tggaaaatat tacgccaaag ttaccgttac gggggggaact    720
ggtaaagatg gctattatga agtttccgtt gataagacga acggtgaggt gactcttgct     780
ggcggtgcga cttccccgct tacaggtgga ctacctgcga cagcaactga ggatgtgaaa     840
aatgtacaag ttgcaaatgc tgatttgaca gaggctaaag ccgcattgac agcagcaggt     900
gttaccggca gcatctgt tgttaagatg tcttatactg ataataacgg taaaactatt      960
gatggtggtt tagcagttaa ggtaggcgat gattactatt ctgcaactca aaataaagat    1020
ggttccataa gtattaatac tacgaaatac actgcagatg acggtacatc caaaactgca    1080
ctaaacaaac tgggtggcgc agacggcaaa accgaagttg tttctattgg tggtaaaact    1140
tacgctgcaa gtaaagccga aggtcacaac tttaaagcac agcctgatct ggcggaagcg    1200
gctgctacaa ccaccgaaaa cccgctgcag aaaattgatg ctgcttttgg cacaggttgac   1260
acgttacgtt ctgacctggg tgcggtacag aaccgtttca actccgctat taccaacctg    1320
ggcaacaccg taaacaacct gacttctgcc cgtagccgta tcgaagattc cgactacgcg    1380
accgaagttt ccaacatgtc tcgcgcgcag attctgcagc aggccggtac ctccgttctg    1440
gcgcaggcga accaggttcc gcaaaacgtc ctctctttac tgcgttggag ccatccgcag    1500
tttgaaaaat aa                                                         1512
```

<210> SEQ ID NO 3
<211> LENGTH: 503
<212> TYPE: PRT
<213> ORGANISM: Salmonella typhimurium
<220> FEATURE:
<221> NAME/KEY: PEPTIDE
<222> LOCATION: (496)...(503)
<223> OTHER INFORMATION: Strep-tag II polypeptide

<400> SEQUENCE: 3

Met Ala Gln Val Ile Asn Thr Asn Ser Leu Ser Leu Leu Thr Gln Asn
1               5                   10                  15

```
Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
                100                 105                 110

Gln Ala Glu Ile Thr Gln Arg Leu Asn Glu Ile Asp Arg Val Ser Gly
            115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
    195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Met Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
    275                 280                 285

Leu Thr Glu Ala Lys Ala Ala Leu Thr Ala Ala Gly Val Thr Gly Thr
    290                 295                 300

Ala Ser Val Val Lys Ile Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
    355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430
```

```
Phe Asn Ser Ala Ile Thr Asn Leu Gly Asn Thr Val Asn Asn Leu Thr
            435                 440                 445

Ser Ala Arg Ser Arg Ile Glu Asp Ser Asp Tyr Ala Thr Glu Val Ser
450                 455                 460

Asn Ile Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Trp
                485                 490                 495

Ser His Pro Gln Phe Glu Lys
            500

<210> SEQ ID NO 4
<211> LENGTH: 1512
<212> TYPE: DNA
<213> ORGANISM: Samonella typhimurium

<400> SEQUENCE: 4
atggcacaag tcattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcgatt gctaaccgtt ttaccgcgaa catcaaaggt     180
ctgactcagg cttcccgtaa cgctaacgac ggtatctcca ttgcgcagac cactgaaggc     240
gcgctgaaca aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggtgcc aacgacggtg aaactatcga tatcgatctg     480
aagcagatca actctcagac cctgggtctg gatacgctga atgtgcaaca aaaatataag     540
gtcagcgata cggctgcaac tgttacagga tatgccgata ctacgattgc tttagacaat     600
agtactttta agcctcggc tactggtctt ggtggtactg accagaaaat tgatggcgat     660
ttaaaatttg atgatacgac tggaaaatat tacgccaaag ttaccgttac ggggggaact     720
ggtaaagatg gctattatga agtttccgtt gataagacga acggtgaggt gactcttgct     780
ggcggtgcga cttccccgct tacaggtgga ctacctgcga cagcaactga ggatgtgaaa     840
aatgtacaag ttgcaaatgc tgatttgaca gaggctaaag ccgcattgac agcagcaggt     900
gttaccggca cagcatctgt tgttaagatg tcttatactg ataataacgg taaaactatt     960
gatggtggtt tagcagttaa ggtaggcgat gattactatt ctgcaactca aaataaagat    1020
ggttccataa gtattaatac tacgaaatac actgcagatg acggtacatc caaaactgca    1080
ctaaacaaac tgggtggcgc agacggcaaa accgaagttg tttctattgg tggtaaaact    1140
tacgctgcag taaagccga aggtcacaac tttaaagcac agcctgatct ggcggaagcg    1200
gctgctacaa ccaccgaaaa cccgctgcag aaaattgatg ctgctttggc acaggttgac    1260
acgttacgtt ctgacctggg tgcggtacag aaccgtttca actccgctat taccaacctg    1320
ggcaacaccg taaacaacct gacttctgcc cgtagccgta tcgaagattc cgactacgcg    1380
accgaagttt ccaacatgtc tcgcgcgcag attctgcagc aggccggtac ctccgttctg    1440
gcgcaggcga accaggttcc gcaaaacgtc ctctctttac tgcgttggag ccatccgcag    1500
tttgaaaaat aa                                                       1512

<210> SEQ ID NO 5
<211> LENGTH: 503
<212> TYPE: PRT
```

-continued

```
<213> ORGANISM: Salmonella typhimurium
<220> FEATURE:
<221> NAME/KEY: PEPTIDE
<222> LOCATION: (496)...(503)
<223> OTHER INFORMATION: Strep-tag II polypeptide
<220> FEATURE:
<221> NAME/KEY: VARIANT
<222> LOCATION: 1
<223> OTHER INFORMATION: Xaa = homopropargylglycine

<400> SEQUENCE: 5

Xaa Ala Gln Val Ile Asn Thr Asn Ser Leu Ser Leu Leu Thr Gln Asn
 1               5                  10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Ile Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
```

```
                355                 360                 365
Gly Lys Thr Glu Val Val Ser Ile Gly Gly Lys Thr Tyr Ala Ala Ser
            370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
            450                 455                 460

Asn Ile Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Trp
                485                 490                 495

Ser His Pro Gln Phe Glu Lys
            500

<210> SEQ ID NO 6
<211> LENGTH: 1512
<212> TYPE: DNA
<213> ORGANISM: Salmonella Typhimurium

<400> SEQUENCE: 6
atggcacaag tgattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggtgcc aacgacggtg aaactatcga tatcgatctg     480
aagcagatca actctcagac cctgggtctg atacgctga atgtgcaaca aaaatataag     540
gtcagcgata cggctgcaac tgttacagga tatgccgata ctacgattgc tttagacaat     600
agtactttta aagcctcggc tactggtctt ggtggtactg accagaaaat tgatggcgat     660
ttaaaatttg atgatacgac tggaaaatat tacgccaaag ttaccgttac gggggggaact     720 ggtaaagatg gctattatga agtttccgtt gataagacga acgtgaggt gactcttgct     780 ggcggtgcga cttccccgct tacaggtgga ctacctgcga cagcaactga ggatgtgaaa     840
aatgtacaag ttgcaaatgc tgatttgaca gaggctaaag ccgcattgac agcagcaggt     900
gttaccggca cagcatctgt tgttaagatc tcttatactg ataataacgg taaaactatt     960
gatggtggtt tagcagttaa ggtaggcgat gattactatt ctgcaactca aaataaagat    1020
ggttccataa gtattaatac tacgaaatac actgcagatat acggtacatc caaaactgca    1080
ctaaacaaac tgggtggcgc agacggcaaa accgaagttg tttctattgg tggtaaaact    1140
tacgctgcaa gtaagccgaa aggtcacaac tttaaagcac agcctgatct ggcggaagcg    1200
gctgctacaa ccaccgaaaa cccgctgcag aaaattgatg ctgctttggc acaggttgac    1260
```

```
acgttacgtt ctgacctggg tgcggtacag aaccgtttca actccgctat taccaacctg    1320
ggcaacaccg taaacaacct gacttctgcc cgtagccgta tcgaagattc cgactacgcg    1380
accgaagttt ccaacatctc tcgcgcgcag attctgcagc aggccggtac ctccgttctg    1440
gcgcaggcga accaggttcc gcaaaacgtc ctctctttac tgcgttggag ccatccgcag    1500
tttgaaaaat aa                                                        1512
```

<210> SEQ ID NO 7
<211> LENGTH: 503
<212> TYPE: PRT
<213> ORGANISM: Salmonella typhimurium
<220> FEATURE:
<221> NAME/KEY: PEPTIDE
<222> LOCATION: (496)...(503)
<223> OTHER INFORMATION: Strep-tag II polypeptide
<220> FEATURE:
<221> NAME/KEY: VARIANT
<222> LOCATION: 1
<223> OTHER INFORMATION: Xaa = Homopropargylglycine

<400> SEQUENCE: 7

```
Xaa Ile Gln Val Ile Asn Thr Asn Ser Leu Ser Leu Leu Thr Gln Asn
 1               5                  10                  15

Asn Leu Asn Lys Ser Gln Ser Ala Leu Gly Thr Ala Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ala Asn Ile Lys Gly Leu Thr Gln Ala
     50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Leu Gln Arg Val Arg Glu Leu Ala
                 85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285
```

Leu Thr Glu Ala Lys Ala Ala Leu Thr Ala Ala Gly Val Thr Gly Thr
            290                 295                 300

Ala Ser Val Val Lys Ile Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
                355                 360                 365

Gly Lys Thr Glu Val Val Ser Ile Gly Gly Lys Thr Tyr Ala Ala Ser
370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
                420                 425                 430

Phe Asn Ser Ala Ile Thr Asn Leu Gly Asn Thr Val Asn Asn Leu Thr
            435                 440                 445

Ser Ala Arg Ser Arg Ile Glu Asp Ser Asp Tyr Ala Thr Glu Val Ser
450                 455                 460

Asn Ile Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Trp
                485                 490                 495

Ser His Pro Gln Phe Glu Lys
            500

<210> SEQ ID NO 8
<211> LENGTH: 1512
<212> TYPE: DNA
<213> ORGANISM: Salmonella typhimurium

<400> SEQUENCE: 8
atgatacaag tgattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggtgcc aacgacggtg aaactatcga tatcgatctg     480
aagcagatca actctcagac cctgggtctg gatacgctga atgtgcaaca aaaatataag     540
gtcagcgata cggctgcaac tgttacagga tatgccgata ctacgattgc tttagacaat     600
agtactttta aagcctcggc tactggtctt ggtggtactg accagaaaat tgatggcgat     660
ttaaaatttg atgatacgac tggaaaatat tacgccaaag ttaccgttac gggggggaact     720 ggtaaagatg gctattatga agtttccgtt gataagacga acggtgaggt gactcttgct     780
ggcggtgcga cttccccgct tacaggtgga ctacctgcga cagcaactga ggatgtgaaa     840

```
aatgtacaag ttgcaaatgc tgatttgaca gaggctaaag ccgcattgac agcagcaggt      900
gttaccggca cagcatctgt tgttaagatc tcttatactg ataataacgg taaaactatt      960
gatggtggtt tagcagttaa ggtaggcgat gattactatt ctgcaactca aaataaagat     1020
ggttccataa gtattaatac tacgaaatac actgcagatg acggtacatc caaaactgca     1080
ctaaacaaac tgggtggcgc agacggcaaa accgaagttg tttctattgg tggtaaaact     1140
tacgctgcaa gtaaagccga aggtcacaac tttaaagcac agcctgatct ggcggaagcg     1200
gctgctacaa ccaccgaaaa cccgctgcag aaaattgatg ctgctttggc acaggttgac     1260
acgttacgtt ctgacctggg tgcggtacag aaccgtttca actccgctat taccaacctg     1320
ggcaacaccg taaacaacct gacttctgcc cgtagccgta tcgaagattc cgactacgcg     1380
accgaagttt ccaacatctc tcgcgcgcag attctgcagc aggccggtac ctccgttctg     1440
gcgcaggcga accaggttcc gcaaaacgtc ctctctttac tgcgttggag ccatccgcag     1500
tttgaaaaat aa                                                         1512
```